US006558620B1

(12) United States Patent
Sanford et al.

(10) Patent No.: US 6,558,620 B1
(45) Date of Patent: May 6, 2003

(54) LIQUID CLEANING AND STERILIZATION METHOD

(75) Inventors: Bill R. Sanford, Willoughby, OH (US); Jude A. Kral, Twinsburg, OH (US); Joseph Tvergyak, Chardon, OH (US); Bernard J. Moss, Willowick, OH (US); Robert M. Priest, Eastlake, OH (US); James C. Hlebovy, Chardon, OH (US); Daniel N. Kelsch, Fairview Park, OH (US); Alan J. Greszler, Elyria, OH (US); David E. Minerovic, Concord, OH (US); John C. Houston, Erie, PA (US); Nancy A. Robinson, Hudson, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/499,561

(22) Filed: Feb. 7, 2000

(51) Int. Cl.$^7$ .................................................. A61L 2/00
(52) U.S. Cl. .................. 422/28; 134/102.2; 134/168 C; 134/170; 422/33; 422/292; 422/300; 422/905
(58) Field of Search ............................ 422/28, 33, 292, 422/300, 905, 110, 119; 134/102.2, 168 C, 170

(56) References Cited

U.S. PATENT DOCUMENTS

| | | |
|---|---|---|
| 1,540,793 A | 6/1925 | Maloney |
| 3,893,843 A | 7/1975 | Fry et al. |
| 4,064,886 A | 12/1977 | Heckele |
| 4,142,539 A | 3/1979 | Shih et al. |
| 4,261,950 A | 4/1981 | Bainbridge et al. |
| 4,281,674 A | 8/1981 | Tanaka et al. |
| 4,333,773 A | 6/1982 | Fjällström |

(List continued on next page.)

FOREIGN PATENT DOCUMENTS

| | | |
|---|---|---|
| EP | 0 269 435 A2 | 11/1987 |
| EP | 0 333 246 A2 | 3/1989 |
| EP | 0 428 009 A1 | 10/1990 |
| EP | 0 835 665 A2 | 10/1997 |
| WO | WO 92/22808 | 12/1992 |
| WO | WO 95/22353 | 8/1995 |
| WO | WO 00/23118 | 4/2000 |

OTHER PUBLICATIONS

W AN assenburg & Co b.v.; Technical Documentation; Cleaning– and disinfection system for endoscopes; machine type/Wassenburg Eds 03; Application/GE; Machine No. 005–. . . (1997).

Primary Examiner—Krisanne Thornton
(74) Attorney, Agent, or Firm—Fay, Sharpe, Fagan, Minnich & McKee, LLP

(57) ABSTRACT

A method of washing, microbially decontaminating, and rinsing of a lumened device (B), such as an endoscope includes positioning the device in a chamber (12) of an automated processor (A). Spray nozzles (102, 104, 106, 108, 110) within the chamber sequentially spray washing, microbial decontaminant, and rinse fluids over the device. Fluid connection ports (150, 152, 154) connect with internal passages (187) of the device for delivering the fluids thereto. Leaking connectors (184) connect the automated processor connection ports with inlet ports (196) of the device and allow a portion of the washing, decontaminant, and rinse solutions to leak from each inlet port. A computer control system (80) controls leak testing, cleaning, decontamination, rinsing, and drying stages of a cycle, which are all carried out within the chamber, obviating the need for human contact with the device during processing. A door locking and latching mechanism (90) ensures that the door remains locked during the washing, decontamination, and rinse cycle to avoid accidental injury to an operator from strong chemicals used in the system.

33 Claims, 14 Drawing Sheets

U.S. PATENT DOCUMENTS

| | | |
|---|---|---|
| 4,410,492 A | 10/1983 | Kaye |
| 4,489,741 A | 12/1984 | Ogasawara |
| 4,527,551 A | 7/1985 | Ishii |
| 4,537,209 A | 8/1985 | Sasa |
| 4,545,956 A | 10/1985 | Ciszewski et al. |
| 4,552,728 A | 11/1985 | Taylor |
| 4,731,222 A | 3/1988 | Kralovic et al. |
| 4,765,963 A | 8/1988 | Mukogawa et al. |
| 4,784,790 A | 11/1988 | Disch et al. |
| 4,862,872 A | 9/1989 | Yabe et al. |
| 4,892,706 A | 1/1990 | Kralovic et al. |
| 4,928,917 A | 5/1990 | Wolf |
| 5,035,752 A | 7/1991 | Tanaka et al. |
| 5,065,350 A | 11/1991 | Fedder |
| 5,090,433 A | 2/1992 | Kamaga |
| 5,120,512 A | 6/1992 | Masuda |
| 5,190,666 A | 3/1993 | Bisconte |
| 5,209,909 A | 5/1993 | Siegel et al. |
| 5,217,698 A | 6/1993 | Siegel et al. |
| 5,225,160 A | 7/1993 | Sanford et al. |
| 5,279,799 A | 1/1994 | Moser |
| 5,288,467 A | 2/1994 | Biermaier |
| 5,310,524 A | 5/1994 | Campbell et al. |
| 5,395,493 A | 3/1995 | Pinkowski |
| 5,400,818 A | 3/1995 | Cosentino et al. |
| 5,425,815 A | 6/1995 | Parker et al. |
| 5,439,654 A | 8/1995 | Kochte |
| 5,492,671 A | 2/1996 | Krafft |
| 5,494,530 A | 2/1996 | Graf |
| 5,494,637 A | 2/1996 | Barlow |
| 5,503,720 A | 4/1996 | Teske |
| 5,505,218 A | 4/1996 | Steinhauser |
| 5,534,221 A | 7/1996 | Hillebrenner et al. |
| 5,552,115 A | 9/1996 | Malchesky |
| 5,558,841 A | 9/1996 | Nakagawa et al. |
| 5,589,005 A | 12/1996 | Ohmi |
| 5,723,090 A | 3/1998 | Beerstecher et al. |
| 5,759,490 A | 6/1998 | Malchesky |
| 5,840,251 A | 11/1998 | Iwaki |
| 5,882,589 A | 3/1999 | Mariotti |
| 5,902,413 A | 5/1999 | Puszko et al. |
| 5,921,256 A | 7/1999 | Barin |
| 6,027,572 A | 2/2000 | Labib et al. |
| 6,068,815 A | 5/2000 | Oberleitner et al. |
| 6,203,767 B1 | 3/2001 | Leasko |
| 6,379,614 B1 * | 4/2002 | Sergio et al. .................. 422/28 |

* cited by examiner

LIQUID CLEANING AND STERILIZATION METHOD

BACKGROUND OF THE INVENTION

The present invention relates to the decontamination arts. It finds particular application in connection with an automated system for leak testing cleaning, sterilizing, and drying devices for medical, dental, mortuary, and pharmaceutical applications, and the like, and will be described with particular reference thereto. It should be appreciated, however, that the invention is also applicable to the decontamination of other devices in an automated processing system.

Medical devices, such as endoscopes, and other lumened instruments, are subjected to thorough cleaning and antimicrobial decontamination between each use. During medical procedures, the devices become coated with blood and other protein-rich body fluids. If the instruments are sterilized while they are coated with these materials, the high temperatures and/or chemicals used in the sterilization process tend to cause the materials to set as a hardened layer of biological residue that becomes difficult to remove. Not only do such residues present a barrier to sterilant penetration, but even when sterilized, they may later break down to form toxic substances which pose hazards to patients when the devices are reused.

Traditionally, such devices are often rinsed in a cleaning solution, such as an enzymatic cleaner, to remove the bulk of the blood and other body fluids from their surfaces. The rinsing process is generally carried out manually by immersing the devices in a shallow tray of the cleaning solution. However, for devices such as endoscopes, the cleaning fluid may not penetrate the length of the internal lumen, leaving a portion of the endoscope to become coated with dried body fluids. Additionally, the biological materials and strong cleaners may pose hazards to personnel coming into contact with them.

High temperature sterilization processes, such as steam sterilization in an autoclave, are generally unsuited to the sterilization of endoscopes because of the delicate components and materials from which they are manufactured. The high temperature and pressure tend to curtail the useful life of endoscopes, rubber and plastic devices, lenses, and portions of devices made of polymeric materials and the like. High temperature sterilization alone does not clean. Any body fluids that are not removed prior to thermal sterilization are typically baked on to the instrumentation.

Instruments which cannot withstand the pressure or temperature of the oven autoclave are often microbially decontaminated with gas, such as ethylene oxide gas or hydrogen peroxide vapor. Like steam, gases do not clean, requiring a separate cleaning operation. The ethylene oxide sterilization technique also has several drawbacks. First, the ethylene oxide sterilization cycle tends to be longer than the steam autoclave cycle. Second, some medical equipment can not be sterilized with ethylene oxide gas. Third, ethylene oxide is highly toxic and can present health risks to workers if not handled properly.

Liquid microbial decontamination systems are now utilized for equipment which can not withstand the high temperatures of steam sterilization. Peroxyacetic acid, or peracetic acid, is a useful sterilant and/or disinfectant for a variety of applications, including disinfection of waste and sterilization or disinfection of medical equipment, packaging containers, food processing equipment, and the like. It has a broad spectrum of activity against microorganisms, and is effective even at low temperatures. It poses few disposal problems because it decomposes to compounds which are readily degraded in sewage treatment plants.

In some situations, a technician mixes a disinfectant or sterilant composition with water and then manually immerses the items to be microbially decontaminated in the liquid composition. The high degree of manual labor introduces numerous uncontrolled and unreported variables into the process. There are quality assurance problems with technician errors in the mixing of sterilants, control of immersion times, rinsing of residue, exposure to the ambient atmosphere after the rinsing step, and the like. For sterilizing large, instruments, such as endoscopes with narrow lumens, however, a large receiving tray and a considerable quantity of decontaminant solution are used to accommodate and fully immerse the instruments.

Integrated decontamination systems, such as peracetic acid decontamination systems, have now been developed which provide a premeasured dose of a decontaminant in solution. Items to be sterilized are loaded into a receiving tray of a sterilization system and a cartridge of concentrated decontaminant inserted into a well. As water flows through the system, the decontaminant, which may be accompanied by surfactants and corrosion inhibitors, is diluted and carried to the receiving tray.

The items to be decontaminated are typically loaded into a treatment chamber through an opening closed by a door. It is desirable to maintain a seal between the door and the chamber, to prevent leakage of potentially hazardous sterilization chemicals from the chamber, and also to prevent ingress of potentially contaminated outside air into the chamber once the items are sterile.

Accidental opening of the door during a sterilization cycle poses hazards to operators because of the strong chemicals generally used. Typically, the door includes hinges along one side and a latch mechanism on the opposing side which holds the door securely against the chamber. With large doors, a single latch is often insufficient to maintain a seal along the length of the door. Having multiple latches increases the time required for opening and closing the chamber.

Spraying the exterior of the instruments, while flowing decontaminant solution through the lumens, would have advantages over full immersion of the devices in reducing the quantity of decontaminant solution used. However, because of the complex shape of endoscopes, the spray jets may not reach all of the surfaces of the device. Additionally, interior surfaces of the lumened devices are not reached by the spray.

The present invention provides for a new and improved automated system for reprocessing endoscopes and the like which overcomes the above-referenced problems and others.

SUMMARY OF THE INVENTION

In accordance with one aspect of the present invention, a method of cleaning and microbially decontaminating a device is provided. The method includes the sequential steps of positioning the device within a chamber, spraying a washing solution over the device from nozzles within the chamber to remove soil from exterior surfaces of the device, spraying a microbial decontaminant solution over the device from nozzles within the chamber to microbially decontaminate the exterior surfaces of the device, and spraying a sterile rinse fluid over the device from nozzles within the chamber to rinse the exterior surfaces of the device.

In accordance with another aspect of the present invention, a method of cleaning and microbially decontaminating an endoscope is provided. The method includes positioning the endoscope within a chamber, contacting the interior surface and the exterior surface of the endoscope with a washing solution to remove soil from the device, then contacting the interior and the exterior surfaces of the endoscope with a microbial decontaminant solution to microbially decontaminate the endoscope. The method further includes contacting the interior and the exterior surfaces of the endoscope with a sterile rinse fluid to rinse the interior and exterior surfaces of the endoscope and then removing the endoscope from the chamber. The contact steps are automatically controlled.

One advantage of the present invention is that an endoscope or other lumened device is cleaned and microbially decontaminated in a single automated process.

Another advantage of the present invention is that hazards posed to personnel by handling contaminated devices are minimized.

Yet another advantage of the present invention is that a leak resistant closure is created with a single latching mechanism.

A further advantage of the present invention is that the door remains locked during a sterilization cycle.

A yet further advantage of the present invention is that a decontaminant delivery system ensures decontamination of all exterior and interior surfaces of the device being decontaminated.

Another advantage of the present invention is that spraying, rather than fully immersing large items, such as endoscopes, reduces the quantities of water and decontaminant, pretreatment agents, and cleaning agents used.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
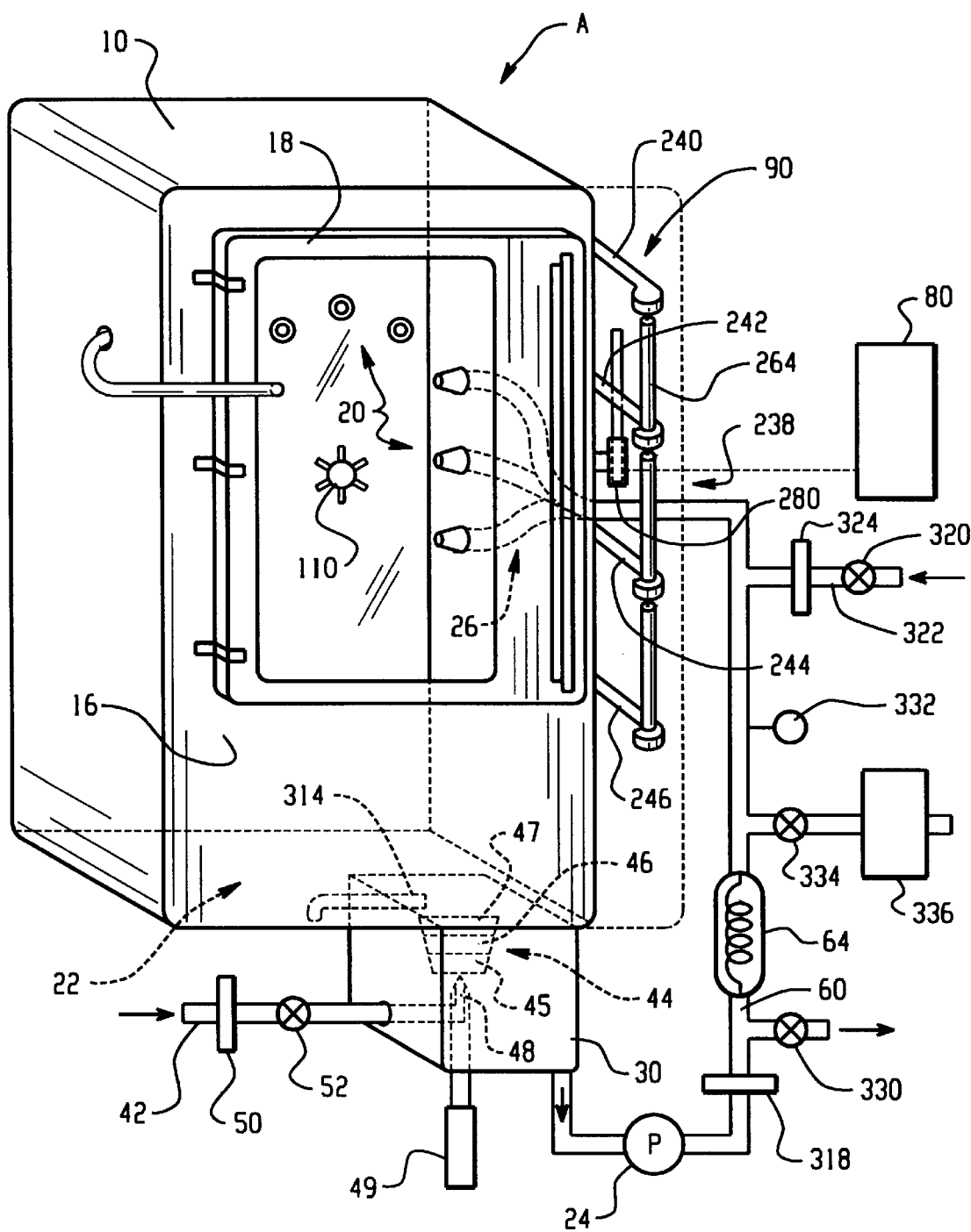
FIG. 1 is a perspective and diagrammatic view of a cleaning and antimicrobial decontamination processor according to the present invention.
Figure 2:
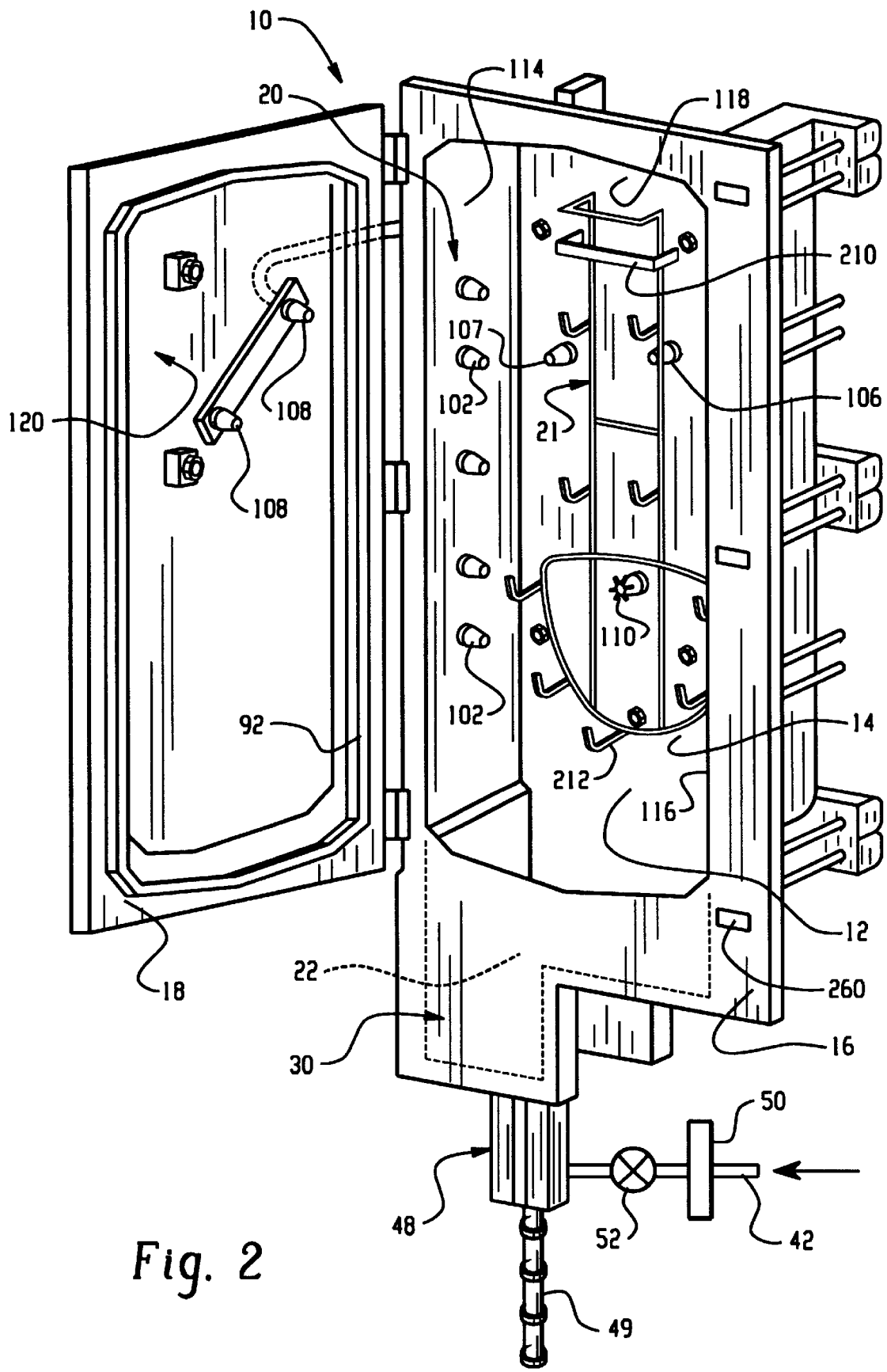
FIG. 2 is a perspective view of the chamber of FIG. 1 with the door open.

With reference to FIGS. 1 and 2, an automated liquid cleaning and antimicrobial decontamination processor or system A sequentially washes then sterilizes or disinfects items, such as medical, dental, and pharmaceutical devices, and the like. While particular reference is made to the cleaning and microbial decontamination of lumened instruments, such as endoscopes, it is to be appreciated that the processor A has application in the cleaning and/or decontamination of a variety of different devices. The processor A is particularly suited to the cleaning and microbial decontamination of instruments which are heat labile, i.e., those, which because of their components or materials, may be damaged by temperatures over about 60° C.

The term "endoscope," as used herein, should be understood to include a wide variety of lumened instruments, including angioscopes, artheroscopes, laparoscopes, bronchoscopes, duodenoscopes, catheters, and the like.

The term "microbial decontamination" and other terms relating to decontaminating will be used herein to describe sterilization, disinfection, and other antimicrobial treatments which are designed to destroy microorganisms contaminating the items. The term "washing" will be used herein to describe the physical removal of soil from the items, without necessarily destroying the microorganisms contaminating the items.

The processor A includes at least one combined washing and microbial decontamination cabinet 10 which defines an interior washing and microbial decontamination chamber 12.

Items to be washed and microbially decontaminated are loaded into the chamber 12 through an opening 14 in a vertical front wall 16 of the cabinet, closed by a door 18. Within the chamber, a fluid distribution system 20, comprising spray jets and connection nozzles, sprays a washing/decontaminant solution over exterior surfaces of the items and directs the solution through internal passages of endoscopes and other objects with lumens. A rack 21 supports one or more endoscopes in a suitable position for optimal effective washing and decontamination by the spray system 20. The endoscope may be loaded on to the rack prior to loading into the chamber, or the rack may be positioned in the chamber prior to attachment of the endoscope.

A collection tank or sump 22 forms the base of the cabinet 10 and receives the sprayed washing/decontaminant solution as it drips off the items. A high pressure pump 24 delivers the washing/decontaminant solution under pressure to the spray system 20 through a fluid distribution system or manifold 26.

A well or mixing chamber 30 sequentially receives doses of a cleaner concentrate and a concentrated decontaminant. The cleaner concentrate mixes with water to form a washing solution for cleaning the items prior to antimicrobial decontamination. The concentrated decontaminant is preferably an antimicrobial agent or comprises reagents which react to form an antimicrobial agent on mixing with water. The cleaner concentrate may be an enzymatic cleaner, or an acid or alkaline cleaner, and may include detergents, surfactants, and the like. A preferred cleaner concentrate is a pH neutral, low foaming composition, which is not harmful to the components of the device. The cleaner concentrate and concentrated decontaminant may be in solid or in liquid form. As shown in FIGS. 1 and 2, the well 30 is integral with the collection tank 22 of the chamber, although a separate well is also contemplated.

A preferred antimicrobial agent is peracetic acid, either in concentrated liquid form, or as a reaction product of powdered reagents, such as acetyl salicylic acid and sodium perborate. A water inlet 42 supplies water, typically from a municipal water system, to the well 30. The water mixes with detergents, corrosion inhibitors, pH buffers, the concentrated decontaminant, and corrosion inhibitor, buffers, and other selected components in the well to form wash, decontaminant, or other solutions.

Preferably, the concentrated decontaminant, cleaner concentrate, and the corrosion inhibitors, buffers, and other components are supplied in a disposable package or cup 44 which is positioned in the well 30 prior to a decontamination cycle. The cup 44 separately holds the measured doses of the concentrated decontaminant and cleaner concentrate, and also a pretreatment mixture of buffers, surfactants, corrosion inhibitors, and other pretreatment chemicals, in separate compartments 45, 46, and 47, respectively, for separate release into the system. In this way, the items are first washed and then microbially decontaminated. A cup cutter 48, driven by an air cylinder 49, or other suitable opening member, is positioned at the base of the well 30 for opening selected compartments of the cup.

The quantity of water entering the system is regulated to provide a washing/decontaminant solution of a desired concentration in the decontamination chamber 12.

The water is preferably passed through a microporous filter in the water inlet line 42, which filters out particles of dirt and microorganisms. A valve 52 in the water inlet 42 closes when the selected quantity of water has been admitted.

Figure 3A:
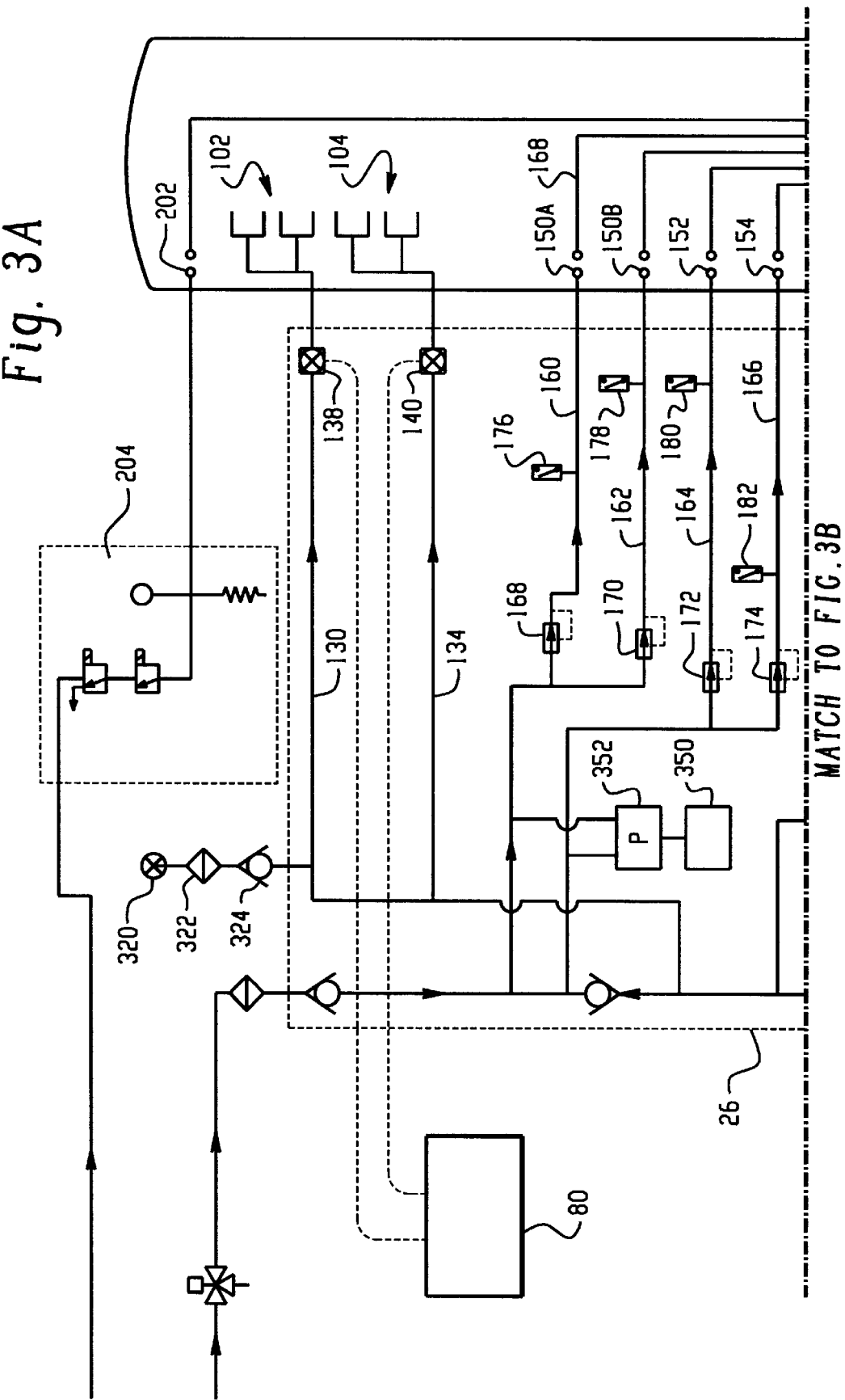
FIG. 3 is a plumbing diagram of the system of FIG. 1.
Figure 3B:
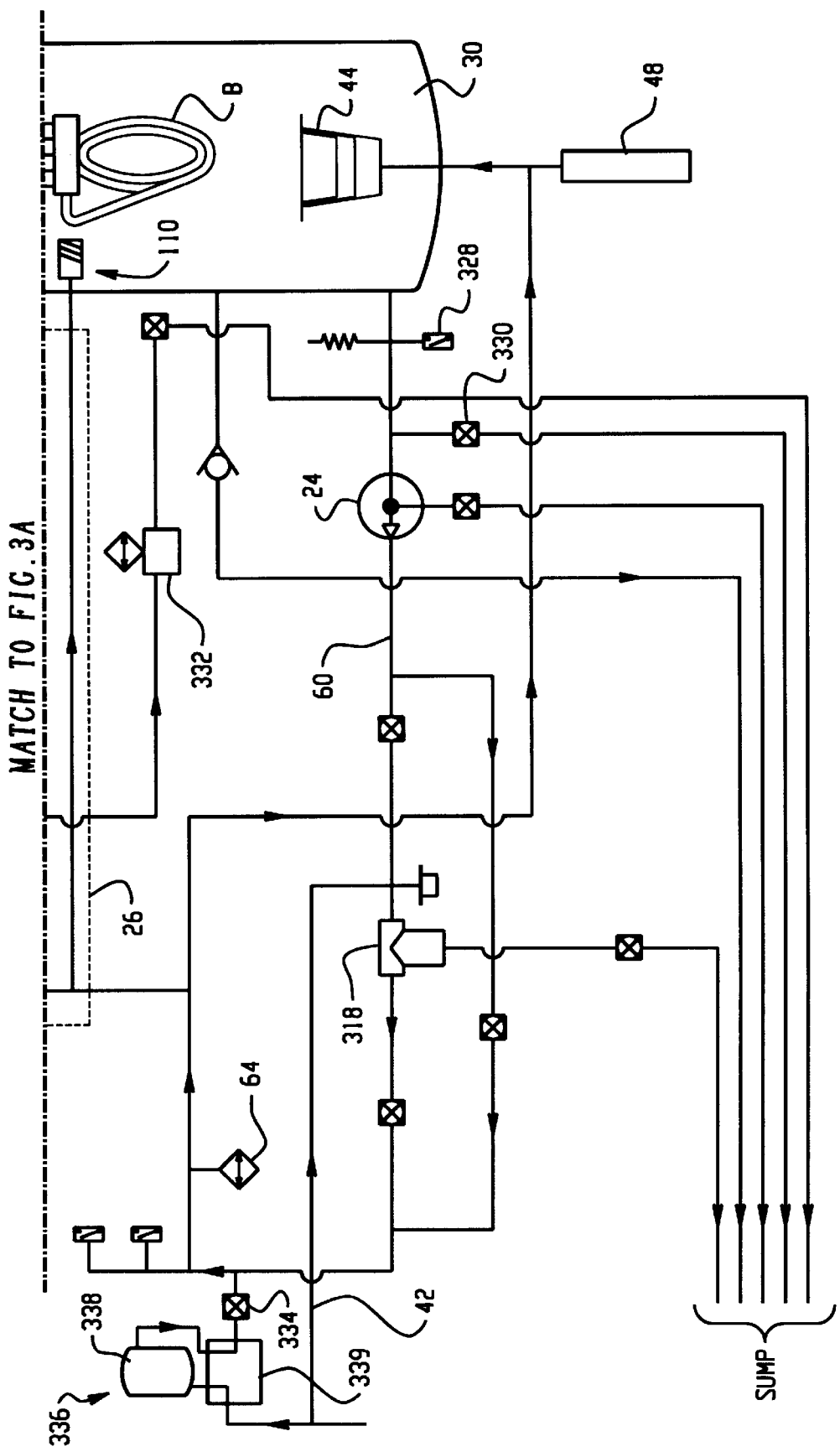

With reference also to FIG. 3, a fluid supply pathway 60 connects the well 30, the pump 24, and the fluid distribution system 26. Thus, a fluid circulation loop is provided which circulates the washing and decontaminant solutions through the well 30, pathway 60, fluid distribution system 26, and spray system 20. Sprayed solutions collect in the well and are pumped by the pump 22 through the pathway, fluid distribution system, and back to the spray system 20. A heater 64, situated in the fluid supply pathway 60, heats the decontaminant solution and optionally the washing solution and a rinse liquid to a preferred temperature(s) for effective cleaning, decontamination, and rinsing.

A computer control system 80 controls the operation of the processor A, including the pump 24, the heater 64, the valves 52, locking of the door 18, and the like. The control system 80 may control one or more additional systems A, if desired.

A door latching and locking mechanism 90 holds the door in the closed position against the front face of the cabinet and prevents the opening of the door during a washing and decontamination cycle. A seal member 92, such as a gasket, it positioned between the door and the front face 16 of the cabinet to provide a fluid tight seal at the pressures used in the cabinet.

Figure 4:
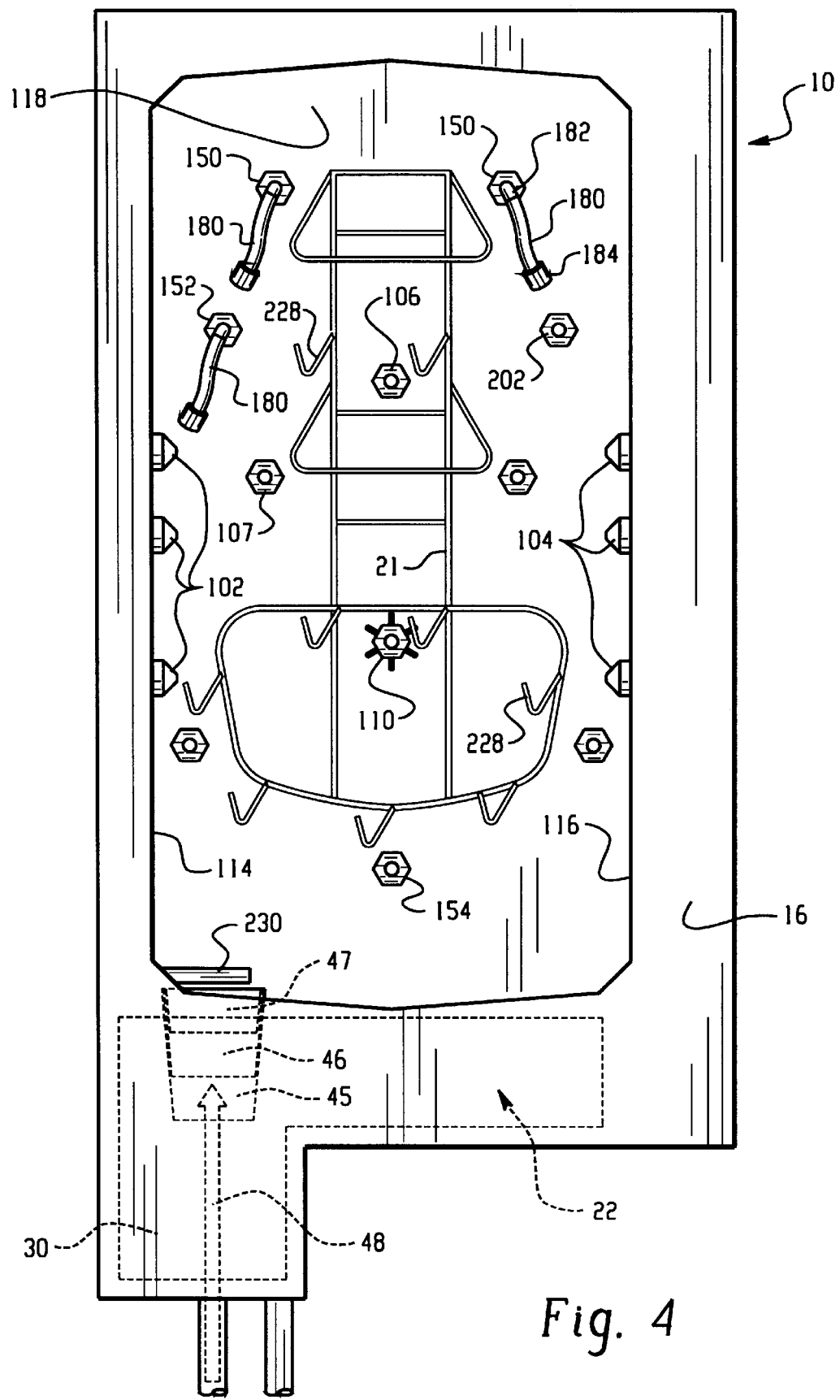
FIG. 4 is a side front view of the chamber of FIG. 2.

With reference to FIGS. 2, 3, and also to FIG. 4, the spray system 20 includes several types of spray nozzles 102, 104, 106, 108, and 110, which direct the cleaning/decontaminant solutions over an endoscope B and other items within the chamber 12 for 360 degree coverage.

The pump supplies the nozzles with the washing/decontaminant fluid at a pressure of about 60–80 psi. The spray nozzles 102 and 104 are located on left and right side walls 114, 116 of the chamber 12, respectively. These have a relatively narrow angle of spray, preferably about 45 degrees, for impacting the surfaces of the endoscope at high pressure. The spray nozzles 106 are located on a rear wall 118 of the chamber. These nozzles spray over a wider angle, preferably about 120 degrees, for wider coverage, although with lesser impact than the nozzles 102, 104. The spray nozzles 108 are attached to an inner surface 120 of the chamber door 18.

The spray nozzle 110 extends forwardly from the rear wall 118 of the chamber and directs cleaning fluid radially in multiple directions for wide coverage. As shown in FIG. 4, the nozzle 110 includes multiple spray heads. Six spray heads are shown, angled at 60 degrees apart, for a 360 coverage. Alternatively, spray nozzle 110 is a rotating nozzle, which is rotated through a 360 degree path to deliver solution in many directions.

Figure 5:
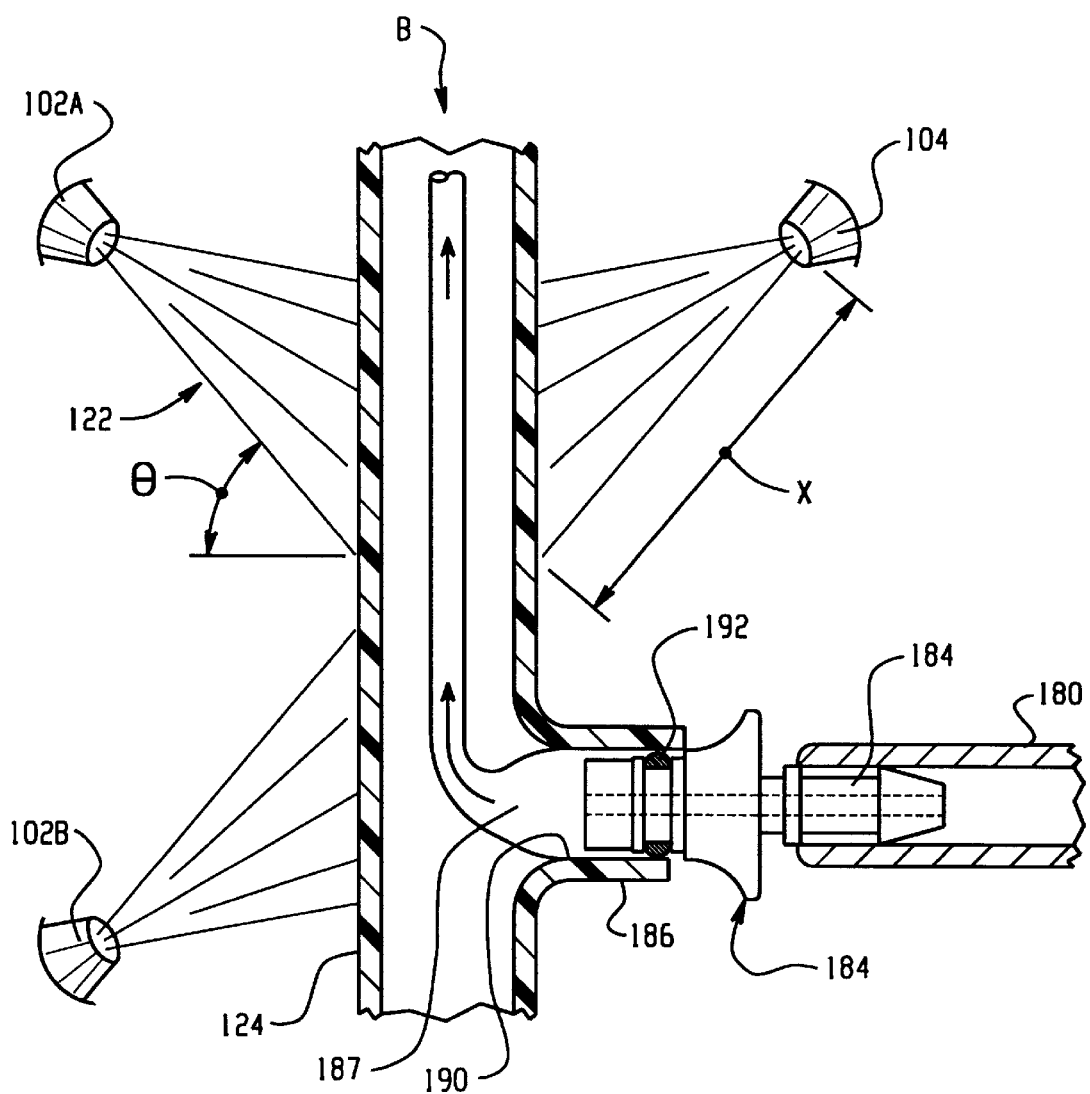
FIG. 5 is a sectional view of a section of an endoscope showing spray jets impinging on its outer surface.

With reference also to FIG. 5, the spray nozzles 102, 104, 106, 108 are angled such that all surfaces of the endoscope B are contacted by the spray of decontaminant solution emitted from the nozzles. Specifically, each nozzle spray jet 122 strikes the endoscope surface 124 at a shallow angle $\theta$, relative to normal to the endoscope surface. Preferably, the angle $\theta$ is less than about 45 degrees, i.e., each surface of the endoscope is struck with at least one spray jet at an angle of no more than about 45 degrees from normal. Thus, the nozzles are angled to deliver the decontaminant/cleaning solutions at different angles. For example, as shown in FIG. 5, nozzle 102A is directed downwardly, while nozzle 102B is directed upwardly. Additionally, each surface of the endoscope is no more than a maximum distance x from the closest spray nozzle, so that the endoscope receives the full force of the spray jet. Preferably, x is no more than 20 centimeters, more preferably, x is less than about 15 centimeters. Further, each surface of the endoscope is no less than a minimum distance from the closest spray nozzle, so that the endoscope receives the full force of the spray jet. Preferably, the minimum distance is at least 5 centimeters.

With reference once more to FIG. 3, to obtain these minimum criteria, the nozzles are in many cases positioned so closely that their sprays may interact. The interaction, prior to contacting the instrument, can negate or alter their force, angle of impact and other characteristics. To avoid the spray jets 122 from different directions canceling each out, the jets are pulsed in sequence. For example, the manifold 26 includes a first fluid line 130 which supplies nozzles 102 and a second fluid line 134 which supplies nozzles 104. The controller 80 sequentially opens an air diaphragm valve 138 in the first line 130 for a few seconds, allowing the cleaning/decontaminant solution to flow to nozzles 102, then opens an air diaphragm valve 140 in the second line 134 for a few seconds, allowing the cleaning/decontaminant solution to flow to nozzles 104.

With reference now to FIGS. 2 and 3, the spray system 20, in addition to the nozzles, also includes several connection ports 150, 152, and 154, for supplying washing/decontaminant solution to the internal passages of the endoscope B and an associated set of biopsy forceps. The different internal passages of a typical endoscope and biopsy forceps are rated to withstand different maximum pressure.

The connection ports supply washing/decontaminant solution at an appropriate pressure that is below the maximum pressure rating for the passage to which the connection port supplies solution. For example, as shown in FIG. 3, the manifold includes fluid lines 160, 162, which supply fluids to connection ports 150A and 150B at a first pressure, preferably of no more than about 20 psi, for washing/decontaminating the lumens, and line 164, which supplies connection port 152 at a second pressure, preferably of no more than about 40 psi, for washing/decontaminating the Endoscopic Retrograde Cholangiopancreatography (ERCP) passages. Another fluid line 166 supplies connection port 154 at a third pressure, preferably of no more than about 20 psi, for cleaning/decontaminating the biopsy forceps. Pressure regulators 168, 170, 172, and 174 in each of the fluid lines 160, 162, 164, and 166 are set to ensure that the maximum pressure is not exceeded. Pressure switches 176, 178, 180, 182 detect whether a minimum fluid pressure in the lines 160, 162, 164, and 166 is met.

With reference once more to FIG. 5, the connection ports 150, 152, and 154 are connected with the respective internal passages of the endoscope and biopsy forceps by tubes 180, each with a quick connect 182 at the connection port end and a suitable connector 184 at the other end for connecting with the inlet port 186 of the respective internal passage, for releasably and quickly connecting the fluid lines with the respective internal passages 187. To avoid confusion and accidental over-pressurization of the lumens, the quick connects 182 for the low pressure lines 160, 162, 166 will not connect with the high pressure connection port 152. In the preferred embodiment, the connectors have different sizing; but, different shapes and the like are also contemplated.

The connectors 184 are preferably leaking connectors, i.e., they allow a controlled portion of the washing/decontaminant solution to flow between the connector and the inlet port to contact all adjacent surfaces 190 of the inlet port 186. This ensures that all the accessible surfaces of the internal passage 187 are contacted with the washing/decontaminant solution. The portion of the washing/decontaminant solution which leaks from around the connector is only a small proportion of the solution entering the inlet port. The majority of the solution travels along the full length of the endoscope internal passage and out of the endoscope into the chamber 12.

In the embodiment of FIG. 5, the leaking connector 184 includes a metal C-ring 191. The C-ring is seated loosely in an annular groove in a portion 192 of the connector which is received past a small lip of the inlet port 186. The ring spaces the connector from the internal surfaces 190 of the inlet port, allowing a portion of the fluid to flow around it and out of the inlet port 186. Other configurations of male and female leaking connectors are also contemplated.

With reference to FIG. 3, a further connection port 202 in the chamber connects a leak detector 204 with the venting connector port of the endoscope for testing the endoscope for leaks. The leak detector supplies air under pressure to the venting connector port and its associated internal passage for detecting leaks from the internal passage. If leaks are found, the leak detector aborts the cycle to prevent fluids from leaking into sensitive regions of the scope.

Figure 6:
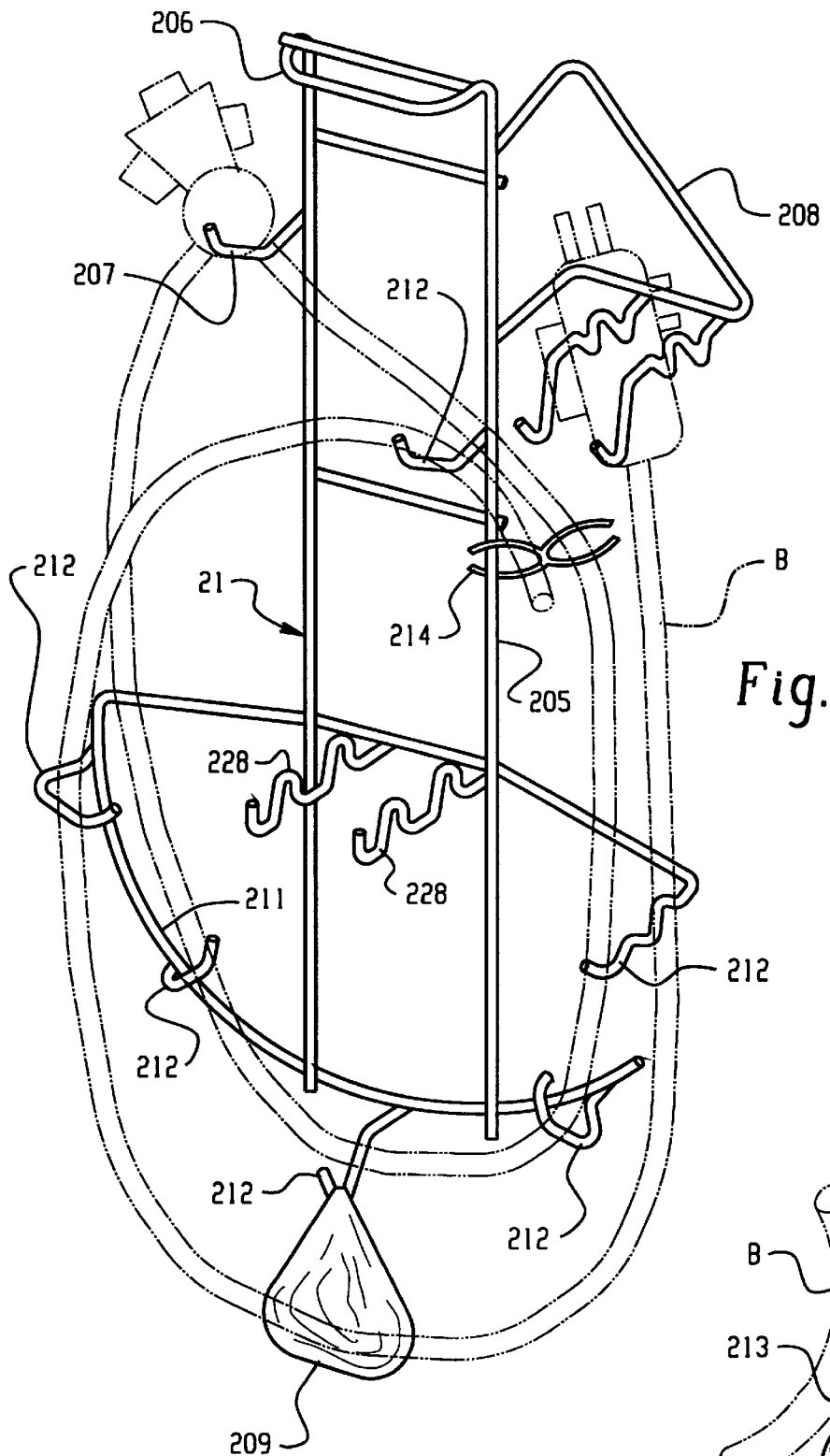
FIG. 6 is a perspective view of the endoscope rack of FIGS. 2 and 4 with an endoscope shown in phantom.

With reference once more to FIG. 2 and reference also to FIG. 6, the rack 21 is preferably removable from the chamber 12. To accommodate different types of endoscope, several racks 21 are provided, each one configured for receiving a particular type or family of endoscopes. The appropriate rack is selected according to the endoscope to be cleaned, and the endoscope fitted to the rack prior to or after hooking or otherwise attaching the rack within the chamber. The rack includes a central rectangular support frame 205 with a carrying and connecting handle 206 attached at an upper end thereof. Mounted on the frame are support members 207, 208, which are configured for receiving the endoscope operating section and light guide connector sections, respectively. Small, separate components of the endoscope, such as hoods, plugs, and other semi-reusable items, may be hung from the rack in a porous bag 209. The upper end of the rack is releasably mounted on a suitably receiving member or members 210 within the chamber.

The rack includes an arcuate portion 211 which supports a number of pegs or tabs 212. The pegs on the arcuate section and the support frame 205 define a circle for support of the flexible tubes (the umbilical cable and the insertion tube) of endoscope B such that the tubes curve in a wide loop on the rack 21. Preferably, the rack and hooks position the endoscope such that it is not bent sharper than its minimum bend radius. In the preferred embodiment, the bend radius is at least 15 centimeters, i.e., no portion of the flexible portions of the endoscope tubes are bent into a curve which has a radius of less than about 15 cm. This ensures that as the endoscope is wrapped around the pegs 212 it is correctly positioned for receiving the full force of the spray jets and that there are no inaccessible or potentially damaging tight bends in the endoscope. Depending on the stiffness of the flexible tube, the tube is mounted inside and/or over the pegs. The pegs are positioned at angular intervals such that the end of the tube of every endoscope in the family ends up near, but just beyond, one of the pegs.

The rack is preferably formed from stainless steel or other materials which are resistant to the decontaminant solution and other chemicals employed in the chamber.

Figure 6A:
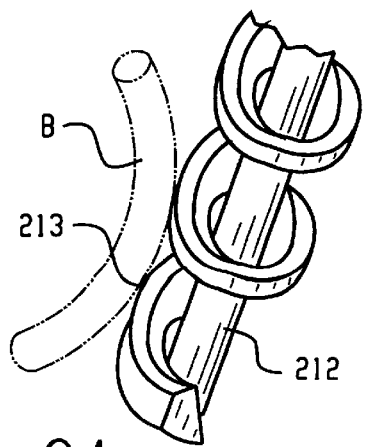
FIG. 6A is an enlarged perspective view in partial section of a rack peg of FIG. 6.

To minimize contact with the endoscope, and improve access of the spray of washing or decontaminating solutions to the contact areas, the support members 207, 208, and pegs 212, preferably make only "point contact" with the endoscope, i.e., the area of contact is as small as is possible, without resulting in damage to the endoscope. In one preferred embodiment, the pegs and support members are formed from a screw-threaded stock, which contacts the endoscope only at tips 213 of the threads, as shown in FIG. 6A. Preferably, the tips of the threads are blunted, such as acme threads or threads with a sinusoidal or other curved cross section, to avoid indentation, scratching, or other damage to the endoscope. A clip 214 holds a tip of the endoscope against the rack.

The rack 21 further includes pegs 228 for supporting coiled biopsy forceps which are designed to pass through a channel of the endoscope. To anchor the forceps more securely, they are preferably coiled on a carrier which is supported on pegs 228.

Figure 7:
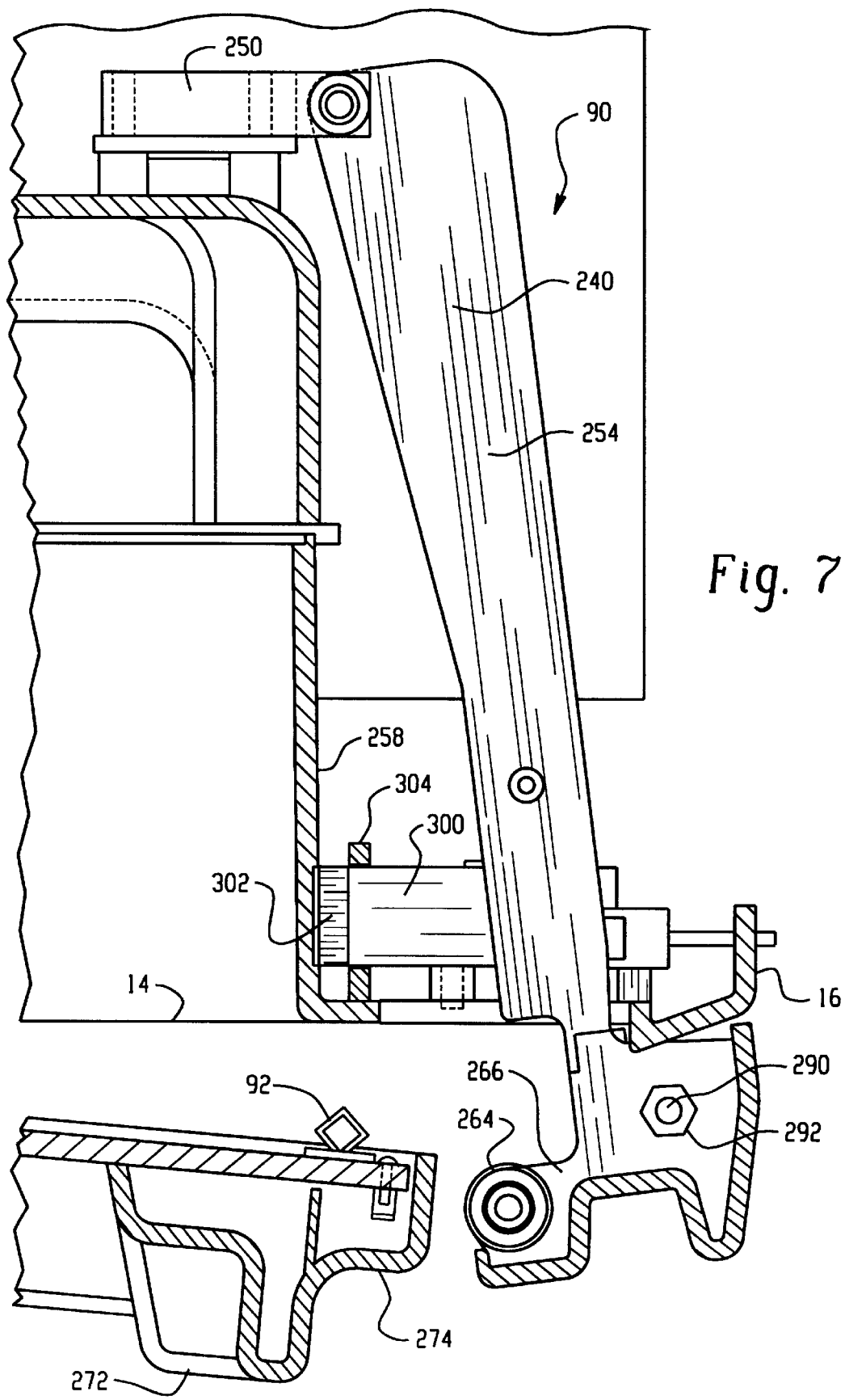
FIG. 7 is an enlarged top view of the door latching and locking mechanism of FIG. 1 with the door partially open.
Figure 8:
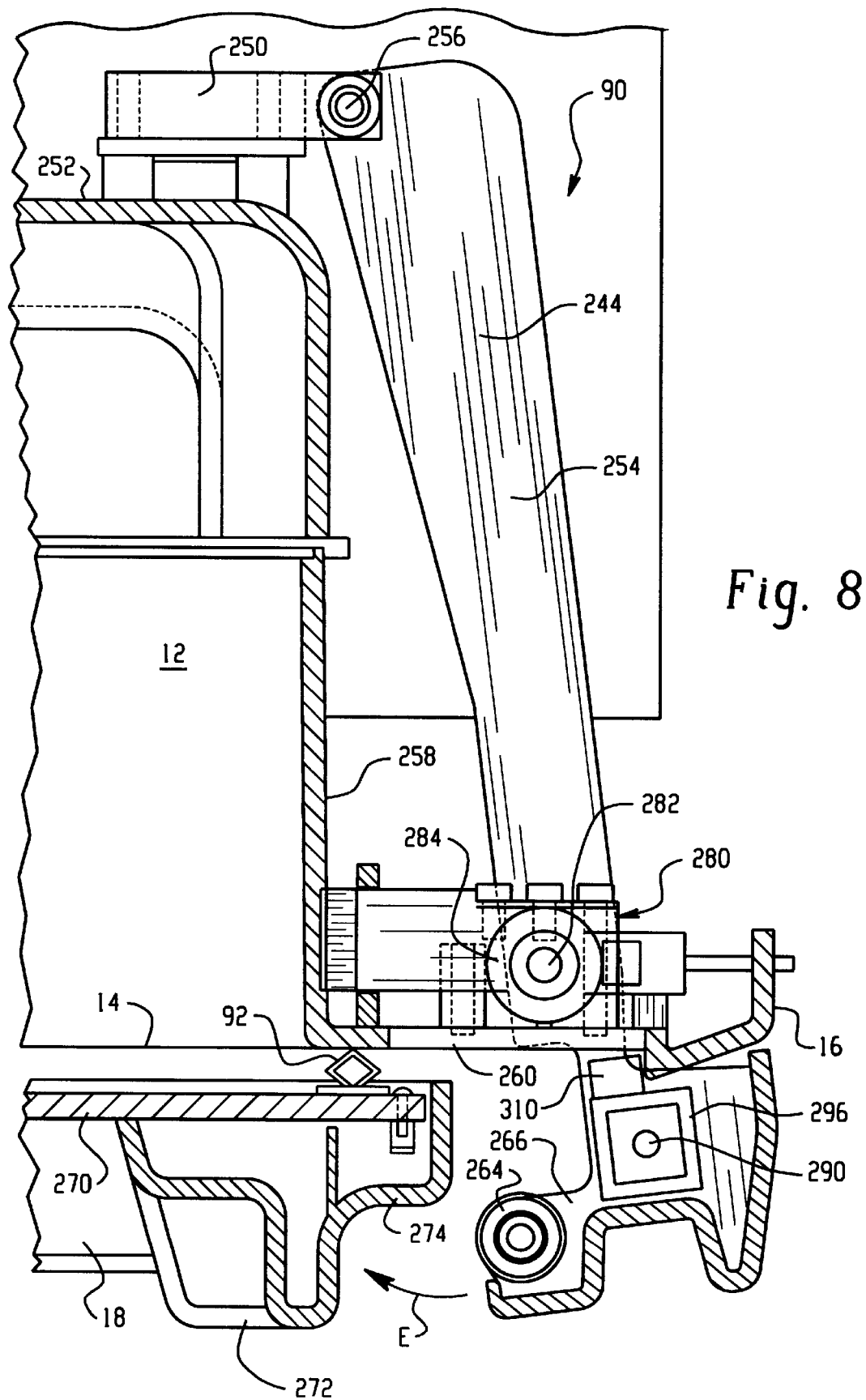
FIG. 8 is a sectional view of the door latching and locking mechanism of FIG. 7 with the door closed.
Figure 9:
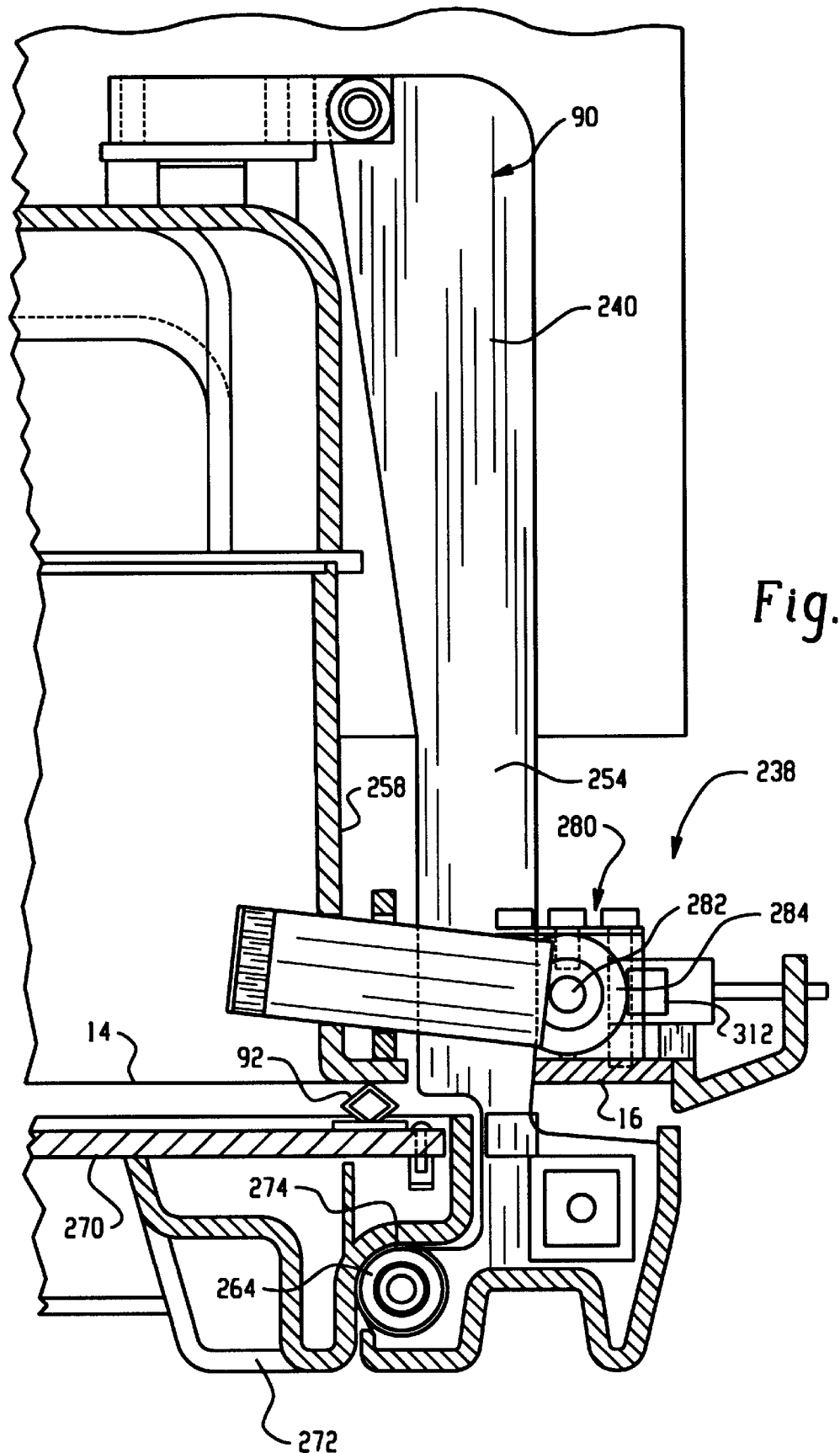
FIG. 9 is a top view of the door latching and locking mechanism of FIG. 7 with the door closed and the latching mechanism engaged.

With continued reference to FIG. 1 and reference also to FIGS. 7, 8, and 9, the door latching and locking mechanism 90 includes a latching mechanism 238, which holds the door 18 closed. The latching mechanism 238 includes at least two and preferably four latching arms 240,242,244,246. Each of the latching arms is pivotally connected to a device 250 which is rigidly mounted to a rear wall 252 of the cabinet. Each of the arms includes a flat plate 254 which is pivotally connected to the clevis at a pivot point 256. The plate 254 extends horizontally forwardly from the pivot point 256, adjacent a side wall 258 of the cabinet. The latching arms 240,242,244,246 extend forwardly of the front face 16 of the cabinet, through suitably positioned slots 260 in the front wall. FIG. 2 shows the slots, but with the latching arms omitted for clarity. One or more rollers 264 (three are shown in FIG. 1) is vertically mounted between pairs of forward ends 266 of the latching arms. The rollers 264 rotate about a vertical axis.

Vertically mounted on a front face 270 of the door, adjacent the door latching mechanism 238, is an engagement member 272 with a vertically extending camming surface 274 having an L-shaped cross section. When the door 18 is in the closed position, as shown in FIG. 8, the latching mechanism 238 can be manually, or automatically pivoted about the pivot points 256 in the direction of arrow E from the disengaged position until the rollers 264 engage the camming surface 274. The camming surface is preferably formed from rubber or other suitable rigid material. In the engaged position (FIG. 9), the rollers 264 hold the door 18 firmly against the front face 16 of the cabinet. In this position, the compression seal 92 is compressed between the door and the cabinet, creating a seal around the opening 14 of the chamber.

Figure 10:
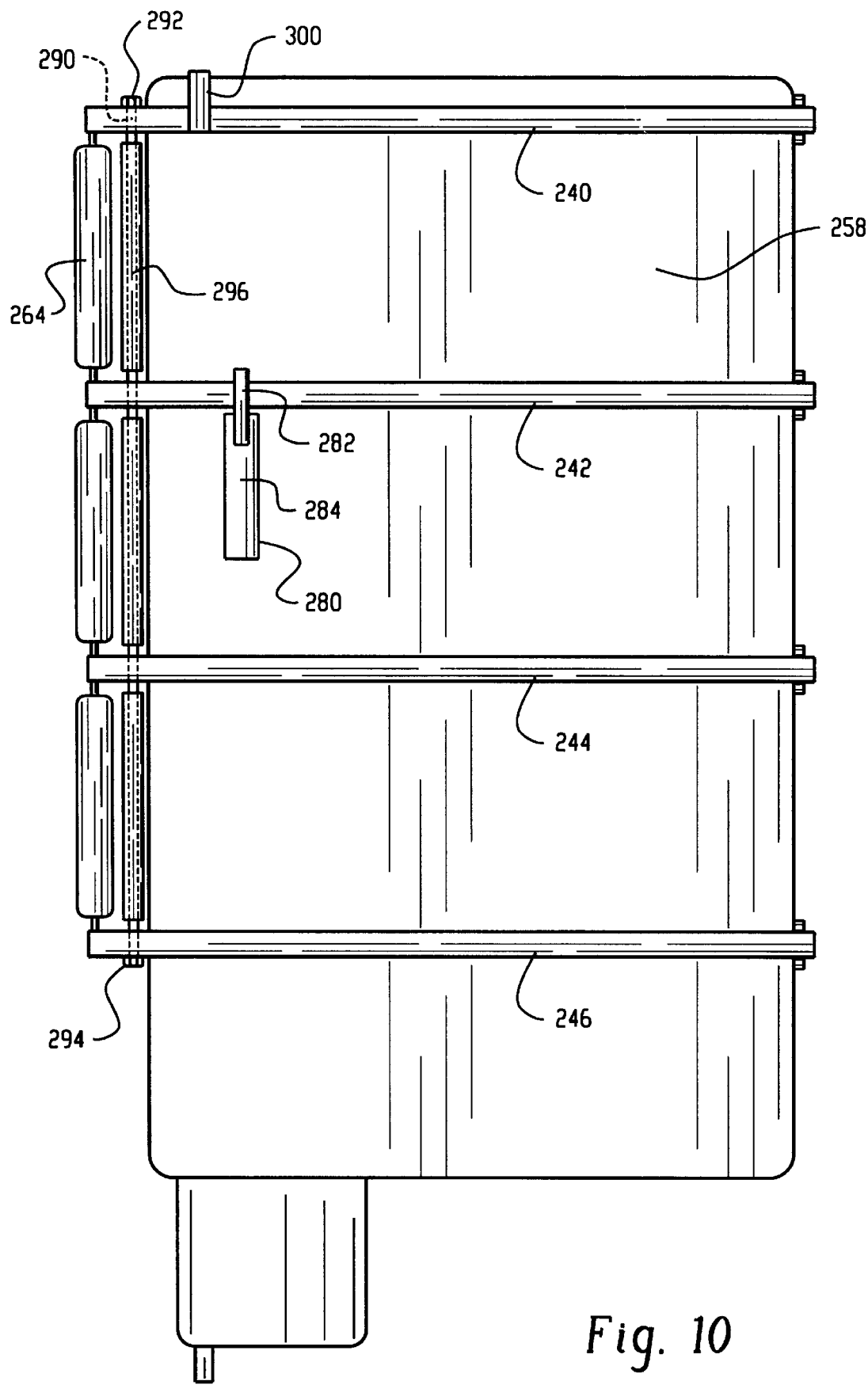
FIG. 10 is a side view of the cabinet of FIG. 1.

With reference to FIGS. 1, 8, 9, and also to FIG. 10, the door latching and locking mechanism 90 also includes a locking mechanism 280, which is actuated by the control system 80 when the latching arms 240,242,244,246 are in the latched position (FIG. 9). The locking mechanism 280 preferably includes a piston rod 282 actuated by an air cylinder 284. In the locked position, the rod 272 extends vertically upward from the air cylinder and engages at least one of the latch arms 242 as shown in FIG. 10. This prevents outward movement of the latch arm and disengagement of the rollers 264 from the engagement member 272. The rod is retracted to an unlocked position before the latching mechanism 238 can be disengaged and the door 18 opened.

Preferably, the latching mechanism 238 includes a supporting member 290, such as a vertically extending wire shaft which connects each of the latching arms 240, 242, 244, 246 together as shown in FIG. 10. The shaft 290 passes through suitably positioned apertures each of the latching arms in turn and is held in tension by upper and lower nuts 292, 294. Blocks 296, each having a central bore, are mounted on the shaft, between pairs of the latching arms, to space the latching arms a suitable distance apart. Thus, the supporting member ensures that each of the latching arms moves generally together, while allowing a limited amount of relative freedom of movement to compensate for minor differences in the width of the door, and the like.

With particular reference to FIG. 7, which shows the door in the partially open position, a latch arm stop 300 is mounted on at least one of the latching arms 240. The latch arm stop 300 extends horizontally from adjacent the forward end of the latching arm, towards the side 258 of the cabinet and includes a downwardly protruding stop 302, formed from rubber or other resilient material. The stop limits the outward movement of the arm by engaging a rearwardly extending flange 304 which is connected to the front wall 16 of the cabinet.

With reference to FIG. 8, a sensor system detects whether the door is properly latched and locked. The sensor system includes a first sensor 310, mounted on the forward end 266 of one of the latching arms, that senses that the latching arm is properly positioned adjacent the engagement member 272. The sensor 310 signals the control system 80 when the sensor is closely spaced from the engagement member 272, as shown in FIG. 9. A second sensor 312 forms a part of the locking mechanism. The second sensor detects whether the piston rod 282 is extended, and therefore engaging the latch arm plate 254, and signals the control system.

In a typical decontamination cycle, items to be decontaminated are first inserted into the cabinet 10 through the opening 14, with the door 18 open, as shown in FIG. 2. The endoscope B to be cleaned is mounted on the rack 21 and inserted into the chamber 12 with other items to be cleaned and decontaminated. The tubes 180 are connected with their respective endoscope inlet ports 186 and connection ports to connect the endoscope internal passages with the fluid lines. The biopsy forceps are loaded on the rack 21. The leak detector 204 is connected with the endoscope venting connector port. A fresh cup 44 of concentrated decontaminant and other components is inserted into the well 30 and a restraining member or lid 314 positioned over the cup.

Once all the items are properly positioned and fluid lines connected, the door 18 is brought into the closed position, as shown in FIG. 8. The latching mechanism 238 is then pivoted around the pivot points 256 until the rollers 264 engage the camming surface 274 as shown in FIG. 9, indicating that the door is fully closed and fully latched. As the latching mechanism is moved from the disengaged to the engaged position, the geometry of the camming surface, the rollers, and the arm pivot point, along with the spring energy provided by the compression seal, result in the final positioning of the rollers being "over center."

The sensor 310, mounted on the forward end of the forward end of the latching arm, senses that the latching arm is properly positioned adjacent the camming surface and signals the control system 80 that the latching mechanism is engaged. The control system then signals the air cylinder 284 to move the piston rod 282 from a lowered, or unlocked position to the locked position, such that the piston rod engages the outer side of the latch arm plate 254. The sensor 312 in the locking mechanism detects that the piston rod is in the locked position, and signals the control system 80 that the latching mechanism is locked in position. The control system does not commence a washing and decontamination cycle until the sensors 310, 312 register that the latching mechanism 238 is properly engaged and that the locking mechanism 280 is in the locked position. At the end of the cycle the control system signals the locking mechanism to retract the locking rod. The latching mechanism can then be withdrawn from engagement with the camming surface.

Figure 11A:
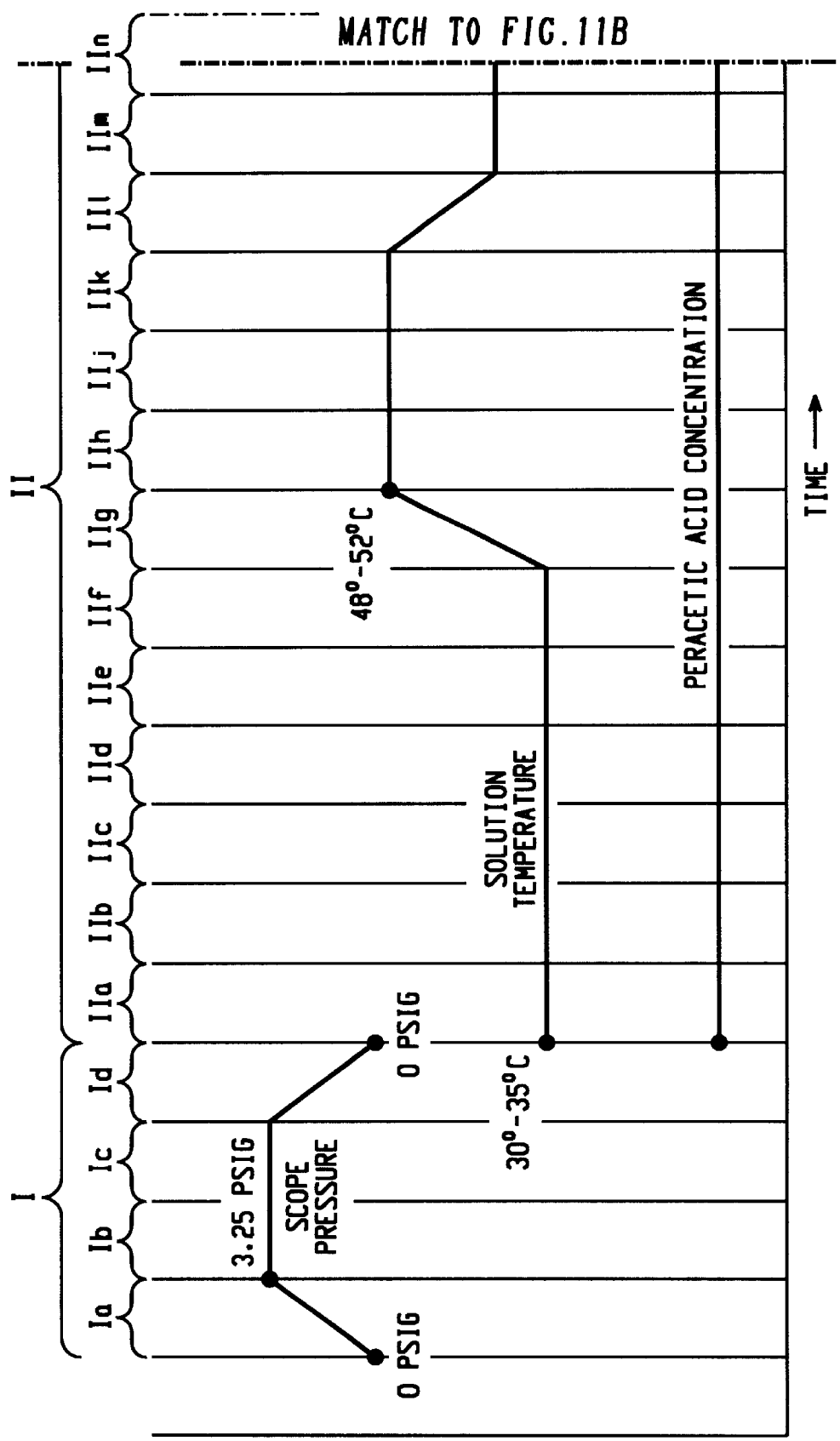
FIG. 11 is a plot showing endoscope pressure, fluid temperature, and peracetic acid concentration with time for a washing and microbial decontamination cycle in the processor of FIG. 1.
Figure 11B:
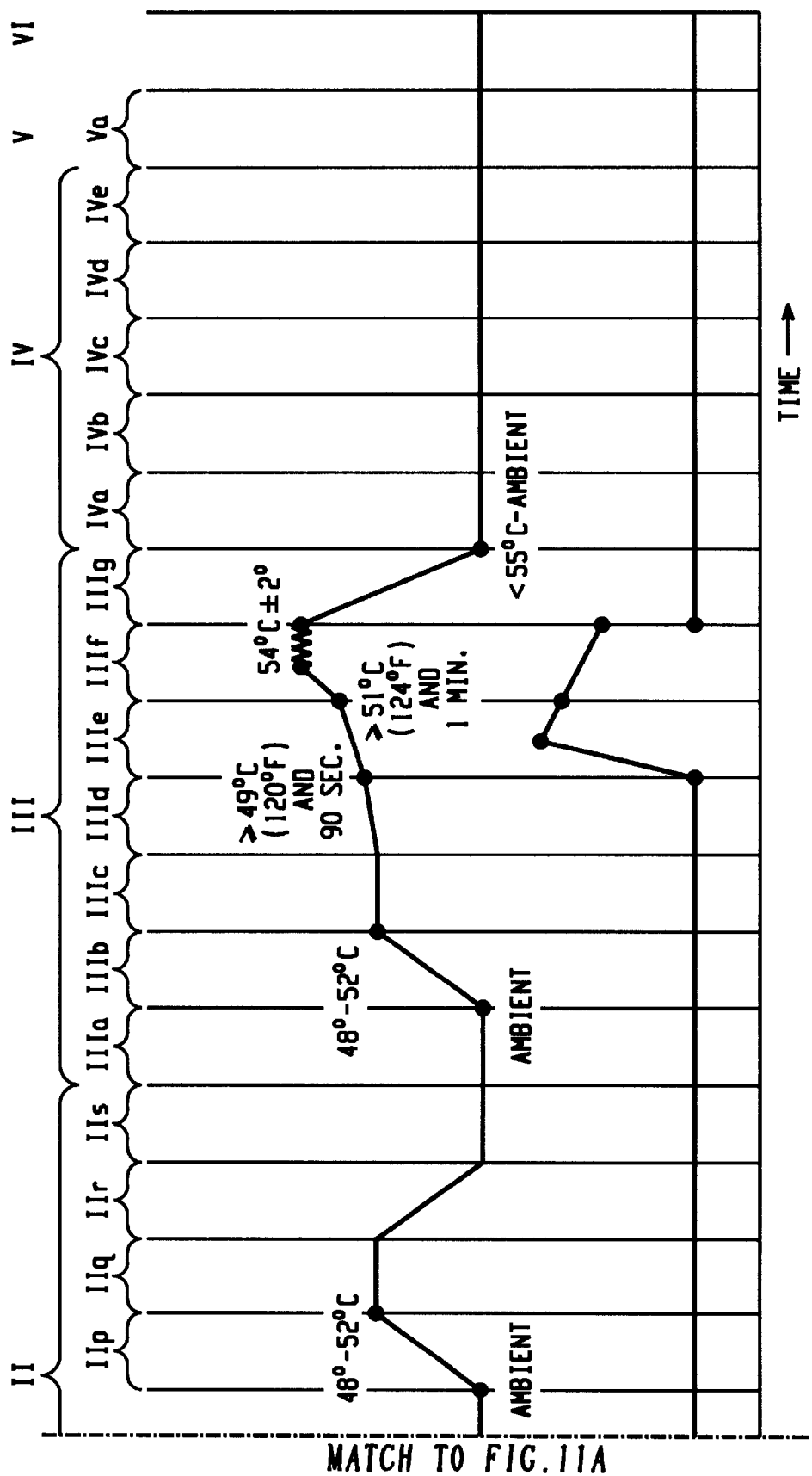

With reference to FIG. 3 and also to FIG. 11, the entire process, including door locking, leak testing, washing, microbial decontamination, and rinsing steps, is fully automated. There is no need for an operator to contact the items until all of the steps are complete. As shown in FIG. 10, a typical cycle includes five phases, a leak testing phase I, a prerinse and washing phase II, a microbial decontamination phase III, a rinse phase IV, and a drying phase V, which are carried out in sequence.

In phase I, the control system 80 signals the leak tester 204 to check the endoscope for leaks. If all is satisfactory, phase II begins. The control system can be programmed to skip this step, if, for example, the device does not have an internal passage to be tested, or if time constraints make it desirable to reduce the overall cycle time.

In phase II, the items are preferably subjected to a prerinse operation, stages IIb–IId, in which the items are sprayed externally and flushed internally with warm (about 30–35° C.) water for about one minute to remove the bulk of surface contamination. The temperature of the water is selected to prevent protein denaturation. Denatured proteins adhere to surfaces and are difficult to remove. Accordingly, the water is kept below 35° C. to prevent this denaturation. All of the soil and other debris which is rinsed off the device is captured in a filter 318, such as a backwashable drain strainer, and is not recirculated through the fluid distribution system. During drain portions of the cycle, the filter is flushed to remove debris.

After about 1 minute of prerinsing, the control system signals a drain valve 240 in the fluid line 60 to open and the rinse water is flushed from the system A to the drain.

In stage IIe, the endoscope is flushed with air. Specifically, the control system 80 signals a valve 320 in an air line 322 to open and supply microbe-free compressed air to the system to remove excess water from the items. The air is preferably passed through a HEPTA microbe removal filter 324 before entering the system.

In stage IIg, the computer control 80 signals the valve 52 in the water inlet line 42 to open, allowing water to circulate through the well and the fluid lines 60. In stage IIh, the heater 64 heats the water to a suitable temperature for cleaning. The temperature selected is within the range of temperature to which the device may be subjected, while providing effective cleaning. For endoscopes which have a maximum rating of 60° C., that are being cleaned with a detergent based washing solution, a preferred washing solution temperature is from about 48–52° C. If an enzymatic cleaner is to be used, the temperature selected will also depend on the stability and operating temperatures of the enzymes employed.

In stage IIj, the computer control system 80 signals the opening member 48 to open the cleaner compartment 46 of the cup. The cleaner concentrate mixes with the water to form the washing solution and is delivered by the pump 22 under pressure to the nozzles 102, 104, 106, 108, 110 and endoscope connection ports 150, 152, 154, 156 in stage IIk. The nozzles spray the washing solution over the outer surfaces of the items while the connection ports deliver the solution to the internal passages, thereby cleaning inner and outer surfaces simultaneously. Sprayed washing solution, which drips off the items, is collected in the sump 22. The pump 22 returns the collected solution from the sump to the fluid supply line 60, preferably after first passing at least a part of the collected solution through the well 30 to ensure complete mixing of the concentrated cleaner in the solution. A sensor 328, such as a conductivity detector detects whether there is concentrated cleaner in the washing solution, for example, by measuring the conductivity of the circulating washing solution.

The washing solution removes soil from the items, leaving them clean, but not necessarily free of viable microorganisms. The spray jets are particularly effective in this physical cleaning stage.

If the instruments to be cleaned have been left for a relatively long period between use and processing (greater than about an hour), it is preferable to use an enzymatic soak prior to, or in place of, the washing phase. This helps to loosen the blood and other proteins, which gradually harden and become difficult to remove. The enzymatic soak preferably lasts from about 10 minutes to about an hour. In the soak, the enzymatic washing solution is circulated slowly through the system. An additional compartment may be provided in the cup 44, if enzymatic cleaning as well as detergent washing steps are to be used. The control system 80 is programmable to provide for an enzymatic soak in place of, or in addition to, a normal washing step.

Once the washing solution has been circulated through the system for sufficient time to remove all or substantially all of the soil from the endoscope and other items the control system signals a drain valve 330 in the fluid line 60 to open and the washing solution is flushed from the processor A to the drain. Optionally, in stage Ill, the water inlet valve 52 is opened to allow additional fresh water into the system to flush the washing solution from the fluid lines 60,24 and the well 30. The drain valve 330 is then closed. Another air flush/drying step is preferably carried out as stage IIm to remove excess water from the items. In stage IIn–s, an additional hot water rinse and dry is optionally carried out.

Optionally, the devices are manually cleaned, rather than being washed in the processor A. In such cases, the operator programs the control system 80 to skip the washing and optionally the rinsing steps IIj–s. A cup 44 which lacks the compartment holding the concentrated cleaning agent is also provided.

In stage IIIa–c, the control system 80 opens the valve 52 for a short period to allow more water into the processor and signals the heater to heat the water. Once sufficient water has entered the system for carrying out the decontaminant part of the cycle, the controller 80 signals the valve 52 to close. The control system 80 signals the cup cutter 48 to open the second compartment 47 of the cup 44, containing the pretreatment components (stage IIId). These are released into the fluid lines and are circulated through the processor as a pretreatment solution. The pump 22 circulates the pretreatment solution so that the pretreatment chemicals are distributed throughout the processor A and over the items to be microbially decontaminated, prior to admission of the decontaminant. The buffers present buffer the water in the fluid lines to an appropriate pH (typically pH 5–9) for effective decontamination. The corrosion inhibitors present coat the parts of the processor to be exposed to the decontaminant solution and the surfaces of items to be decontaminated with traces of inhibitors to provide resistance to the corrosive effects of the decontaminant.

Although the pretreatment components may be alternatively included in one or other of the cleaner and decontaminant compartments 46,45 their effectiveness is less there than if used as intermediate pretreatments. If the pretreatment components are not released into the processor A prior to the decontaminant, for example, they do not have time to circulate through the system prior to addition of the microbial decontaminant. In the case of inhibitors, for example, their function is to provide protection for the system, and items to be microbially decontaminated, against the corrosive components of the microbial decontaminant. By releasing corrosion inhibitors before the microbial decontaminant, the inhibitors are assured time to develop protective barriers around the parts before the parts are contacted by the decontaminant. In the case of buffers, their function is to modify the pH of the fluid circulating in the system so that the pH is optimal for microbial decontamination, again near neutral with a preferred pH of 5–9. Until the buffer has circulated throughout the system, the microbial decontaminant is not fully effective. Additionally, such agents may degrade the microbial decontaminant during storage. Accordingly, it is preferable to provide a separate compartment 47 for the pretreatment components and allow them to circulate through the system for a period of time before introducing the decontaminant.

After a preselected period of circulation, the controller 80 signals the cutter assembly to open the third compartment 45 (stage IIIe). The decontaminant then mixes with the pretreatment components in the fluid lines 60, 24 and is sprayed through the nozzles 102, 104, 106, 108, 110 and delivered to the endoscope connection ports 150, 152, 154, 156, so that the decontaminant solution flows over the exterior surfaces and through the internal passages of the items to be decontaminated (stage IIf). The nozzles pulse the decontaminant fluid in a preselected sequence to ensure full coverage of the spray. A decontaminant sensor 332 in fluid communication with one of the fluid flow lines 60, 24 optionally detects the concentration of the decontaminant in the circulating fluid to ensure that a threshold concentration for effective decontamination is provided.

The control system controls the heater so that an optimum temperature for decontamination is maintained. Once again, the optimum temperature is dependent on the maximum rating for the device being decontaminated, and also on the effective temperature for the decontaminant. For peracetic acid sterilization of endoscopes rated to 60° C., a preferred minimum temperature of about 48–55° C., more preferably, about 50° C., for the circulating decontaminant solution is maintained.

The chamber is maintained under a slight positive pressure during decontamination to minimize ingress of outside air into the chamber. Air exits the chamber through vents (not shown), which provide a tortuous pathway to minimize air ingress.

After a period of circulation of the decontaminant solution sufficient to effect decontamination of the items (typically about 10–15 minutes for complete sterilization, more preferably, about 12 minutes; 2–5 minutes for high level disinfection, more preferably, about 3 minutes), the drain valve 330 in the processor A is opened and the decontaminant solution flushed from the processor A to the drain (stage IIIg). The circulation period is optionally adjusted in accordance with monitored decontaminant levels during the cycle.

The rinse phase IV then begins. The drain valve 330 is kept open and the control system opens a valve 334 to allow a source 336 of sterile rinse water to supply sterile water to the fluid lines 60 for rinsing the decontaminated items without risk of recontamination of the decontaminated items. The source of sterile water preferably comprises a water heater 338 which heats incoming tap water to a sufficient temperature to destroy microorganisms (preferably about 150° C.) in the water, and a heat exchanger 339, which transfers excess heat from the sterilized water to the incoming tap water (FIG. 3). The water heater removes salts from the incoming water which could otherwise deposit on the washed and microbially decontaminated instruments. The water produced by the sterile water generator is thus of high purity. The sterile water generator 336 provides water on demand, eliminating the need to store large quantities of sterile water. The rinse phase may include several fill and blow off stages (IVa–e).

Alternatively, the water inlet valve 52 is opened once more to provide rinse water for rinsing the decontaminated items again.

The system A has a fill of about 9 liters. A typical cycle includes 6 fills, for a total fluid requirement of 54 liters, as follows:

1) for pre-rinsing,
2) for forming the washing solution,
3) rinsing the washing solution from the system,
4) for forming the pretreatment and decontaminant solution, and
5) and 6) for sterile rinsing.

After the rinse water has been discharged to the drain, the control system 80 signals the valve 320 in air line 322 to open and supply microbe-free air to the system to blow accumulated water out of and of f of the decontaminated items. The air line is connected with the manifold 26 so that the air flows through the nozzles and connection ports, drying the interior and exterior surfaces of the endoscopes and other items. The regulator valves 168, 170, 172, and 174 ensure that the internal passages of the endoscope B are not pressurized beyond their recommended pressure ratings.

Optionally, an alcohol flush is used in addition to, or in place of the last of the rinse steps IV a–e. In this case, a source of alcohol 350 supplies the alcohol to the chamber to remove excess water from the device B. Remaining alcohol quickly evaporates from the device. FIG. 3 shows the source of alcohol connected with the connection ports 150, 152, 154, via a pump 352 for delivering the alcohol to the internal lumens of the device, although it is also contemplated that the alcohol may be supplied to the nozzles also, for drying the exterior of the device.

Optionally, the device may be kept in the chamber for an extended period, such as overnight, to increase water removal. Or the air used to flush the device may be heated to increase evaporation and water removal.

At the end of the cycle (stage VI), the controller 80 signals the cutter assembly 48 to retract from the cup 44 to its starting position and the door locking mechanism to disengage.

Because the steps of leak testing, washing, decontaminating, rinsing, and air drying are carried out automatically and sequentially within the chamber, the entire reprocessing cycle can be carried out in a relatively short period of time, typically 30 to 40 minutes for full sterilization, 20–30 minutes for high level decontamination. The endoscopes are thus ready for reuse in a much shorter time than conventional cleaning and decontamination processes, in which an operator carries out the reprocessing steps using a number of separate pieces of equipment.

The decontaminated items are removed from the decontamination chamber 12 for immediate use or transferred to sterile pouches and stored until needed. The rack 21 can be used to transport the endoscope B to a storage cabinet or to a surgery. The rack handle is configured for carrying the rack and for supporting the rack in the storage cabinet. Thus, the endoscope need not be touched until it is to be used in a surgical procedure, minimizing the potential for contamination.

Optionally, the device B is enclosed in a sterile pouch before removal from the chamber, to minimize airborne contamination prior to reuse. For example, the device may be wrapped in a bag, within the chamber, prior to opening of the door. This may be achieved by suitable controls, or manually, for example with a glove box-type of device in which the operator removes the various connectors from the device and wraps the device in the bag using sterile gloves (not shown) which extend into the chamber.

In an alternative embodiment, the chamber 12 acts as a sterile pouch and is hermetically sealed and disconnected from the rest of the processor A and transported to the site at which the decontaminated items are to be used.

Figure 12:
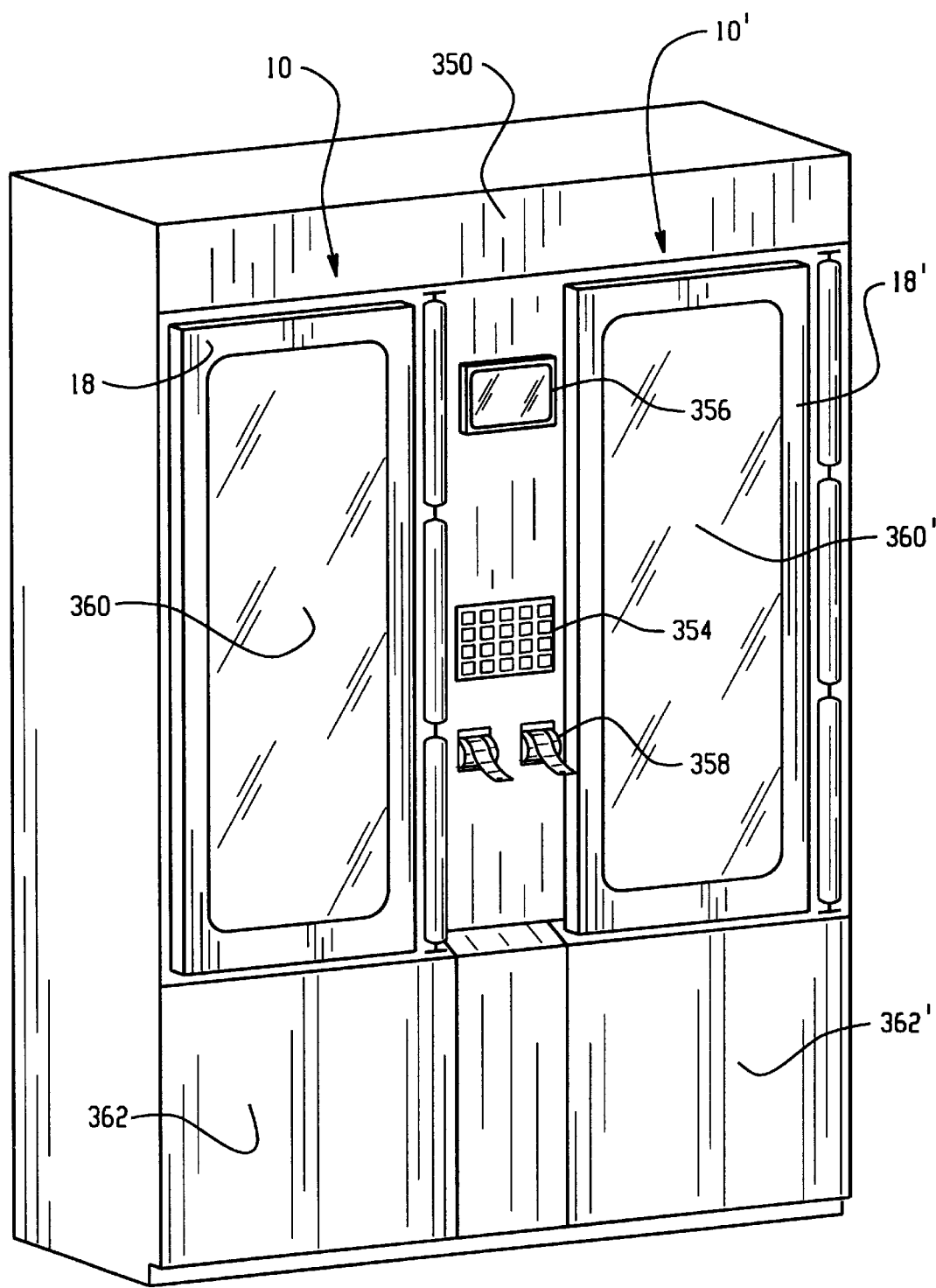
FIG. 12 is a perspective view of a twin cabinet embodiment of a processor in accordance with the present invention.

With reference to FIG. 12, a pair of the cabinets 10, 10' are mounted side by side in a common frame 350. A control panel 352 for controlling the cycles in both cabinets is disposed between the two cabinets. The control panel includes a touch input device 354, such as a touch screen or key pad, which an operator selects among the cycle options and inputs other commands to the control system 80. The control system controls the cycles in each cabinet independently, allowing cycles to be run asynchronously. An electronic display 356 provides real time information to the operator about the state of the system and cycles in progress.

A pair of printers provide printouts 358 descriptive of each sterilization cycle. The printout is available to be transported with the decontaminated endoscope for record keeping purposes. Preferably, an electronic record is also maintained.

The cabinets 10, 10' each have doors 18, 18' that include large see-through windows 360, 360'. These windows enable the operator to monitor the inside chambers of the cabinets during and between cycles. The frame 350 includes door panels 362, 362' that provide front access to water filters and other service items.

Suitable concentrated cleaning agents are low foaming detergents or enzymatic cleaners, with a pH close to neutral (preferably pH 6–8), to minimize corrosion of metal components.

Various antimicrobial agents may be utilized for the decontaminant. In a preferred embodiment, the decontaminant is a solution of peracetic acid. However, it is also contemplated using other liquid or powdered decontaminants or reagents which react in a common solvent to generate peracetic acid, chlorine, hydrogen peroxide, hypochlorous acid, hypochlorite, or other strong oxidants which have biocidal effects. Aldehydes, such as glutaraldehyde, may be used, but the decontaminant solution should be collected after use and properly treated, rather than disposed of via the drain.

Preferably, the pretreatment agent includes a buffer and a corrosion inhibitor. One preferred buffering system includes a combination of monosodium phosphate, disodium phosphate and tripolyphosphates. Such a buffering system also provides anticorrosion properties. Wetting agents and other corrosion inhibitors may alternatively be used. Preferred copper and brass corrosion inhibitors include azoles, benzoates, other five-membered ring compounds, benzotriazoles, tolytriazoles, mercaptobenzothiazole, and the like. Other anti-corrosive compounds include phosphates, molybdates, chromates, dichromates, tungstates, vanadates, borates, and combinations thereof.

The corrosion inhibitory agents are selected in accordance with the nature of the materials in the items being cleaned and/or decontaminated with the decontaminant. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and ortho-phenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$).

Copper and brass corrosion inhibitors include triazoles, azoles, benzoates, tolytriazoles, dimercaptothiadiazoles, and other five-membered ring compounds. Particularly preferred copper and brass corrosion inhibitors include sodium salts of benzotriazole and tolyltriazole which are preferred due to their stability in the presence of strong oxidizing compounds. Mercaptobenzothiazole can also be utilized but is apt to be oxidized or destabilized by strong oxidizers. Salicylic acid is an example of an acceptable benzoate corrosion inhibitor.

In hard water, phosphate buffers and corrosion inhibitors tend to cause calcium and magnesium salts present in the hard water to precipitate and coat the instruments being decontaminated and/or cleaned and also leaves deposits on parts of the system. In such cases, a sequestering agent appropriate to prevent precipitation such as sodium hexametaphosphate (HMP), or trisodium nitrolotriacetic acid (NTA $Na_3$) is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated. However, to ensure universal applicability with any water that might be utilized, the presence of a sequestering agent is preferred.

A surface energy reducing agent (surfactants/wetting agents) is preferably agents to increase penetration into crevices of items being treated. This is particularly important when cleaning and decontaminating complex medical instruments which may contain microbial contaminants in crevices, joints, and lumens. Surface energy reducing agents usable in accordance with the present invention include anionic, cationic, nonionic, amphoteric, and/or zwitterionic surfactants. Specific classes of surfactants which are useful include anionic and nonionic surfactants or combinations thereof. Examples of nonionic surfactants usable in the present invention include surfactants such as fatty alcohol polyglycol ethers, nonylphenoxypoly (ethyleneoxy) ethanol, and ethoxylated polyoxypropylene. Specific examples include Genapol UD-50™, Igepal™, Fluowet™, and Pegal™. The surfactants set forth above may be used alone or in combination with each other.

Amounts of the corrosion inhibitors and surfactants to be used in the peracetic acid solution will vary depending upon the type of agent being added and whether or not one or more agents are added.

The inorganic corrosion inhibitors are preferably present in amounts ranging from about 0.01% to 20.0% weight per volume (w/v). Organic corrosion inhibitors are preferably present in amounts ranging from about 0.01% to 5.0% w/v. Phosphates are effective at concentrations in the range of about 0.01% to about 11.0% w/v.

The surfactants are preferably present in amounts ranging from about 0.0001% to about 5.0% w/v. More preferably, the surfactant is present in amounts ranging from about 0.0001% to about 0.5% w/v.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of cleaning and microbially decontaminating a device comprising the sequential steps of:
   (a) positioning the device within a chamber;
   (b) spraying a washing solution over the device from nozzles within the chamber to remove soil from exterior surfaces of the device; and
   (c) alternately spraying a microbial decontaminant solution over the device from a first group nozzles within the chamber urging the device in one direction and spraying microbial decontaminant solution over the device from a second, differently directed group of nozzles urging the device in another direction to expose and microbially decontaminate the exterior surfaces of the device.

2. The method of claim 1, further including between steps (a) and (b):
   leak testing at least one internal passage of the device, continuing with step (b) only in response to passing the leak test.

3. The method of claim 1, wherein the device is an endoscope having internal lumens, step (a) further including:

coiling the endoscope into the chamber;

connecting a first internal lumen of the endoscope with a liquid supply port and a second internal lumen with a leak test port;

leak testing the device connected to the leak test port.

4. The method of claim 3, further including in response to passing the leak test;

rinsing the endoscope with water to remove debris; and draining the rinse water.

5. The method of claim 1, wherein step (b) includes:

mixing a cleaner concentrate with water to form the washing solution;

concurrently with spraying the endoscope exterior with the washing solution, circulating the washing solution through at least one interior lumen of the device; and draining the washing solution.

6. The method of claim 1, further including after step (b):

draining the washing solution;

spraying rinse water over the exterior of the endoscope and circulating the rinse water through a first internal lumen; and draining the rinse water.

7. The method of claim 5, further including:

after draining the rinse water, blowing microbe-free air through the at least one lumen.

8. The method of claim 1, wherein step (c) includes:

mixing a microbiocidal compound with water to form the microbial decontaminant solution;

concurrently with spraying the microbial decontaminant solution over the endoscope, circulating the microbial decontaminant solution through a lumen of the device connected with a liquid supply port; and draining the microbial decontaminant solution.

9. A method of cleaning and microbially decontaminating an endoscope having at least a first lumen comprising the sequential steps of:

(a) positioning the endoscope within a chamber;

(b) spraying a washing solution over the endoscope from nozzles within the chamber to remove soil from exterior surfaces of the endoscope;

(c) spraying a microbial decontamination solution over the endoscope from nozzles within the chamber to microbially decontaminate the exterior surfaces of the endoscope;

(d) flowing a microbial decontamination solution through the interior passage from a connector which is releasably connected with an inlet port to the lumen to microbially decontaminate the lumen;

(e) passing a fraction of the microbial decontamination solution from the connector into the chamber, the fraction passing between the connector and the inlet port of the endoscope adjacent the lumen to kill any microbes lodged between the connector and the inlet port.

10. The method of claim 9, further including:

after step (e), concurrently spraying sterile rinse water over the endoscope and circulating the sterile rinse water through the first lumen; and draining the rinse water.

11. The method of claim 10, further including:

while draining the rinse water, blowing microbe-free air at least through the first lumen.

12. The method of claim 10, further including after draining the rinse water:

spraying the endoscope exterior with alcohol and circulating alcohol through the first lumen; and draining the alcohol.

13. The method of claim 12, further including:

while draining the alcohol, blowing microbe-free air at least through the first lumen.

14. A method of cleaning and microbially decontaminating first and second devices comprising the sequential steps of:

(a) mounting the first device within a first chamber and mounting the second device in a second chamber;

(b) spraying a washing solution over the first and second devices from nozzles within the first and second chambers to remove soil from exterior surfaces of the devices;

(c) spraying a microbial decontaminant solution over the first and second devices from nozzles within the first and second chambers to microbially decontaminate the exterior surfaces of the first and second devices;

(d) spraying a sterile rinse fluid over the first and second devices from nozzles within the first and second chambers to rinse the exterior surfaces of the first and second devices;

(e) with a common controller, causing steps (b), (c), and (d) to be performed independently and asynchronously in the two chambers.

15. The method of claim 9, further including:

(e) delivering the washing solution to the lumen of the endoscope to remove soil from the lumen of the device; and (f) delivering the microbial decontaminant solution to the lumen of the endoscope to microbially decontaminate the lumen of the endoscope.

16. A method of step cleaning and microbially decontaminating a device with an internal passage, comprising the sequential steps of:

(a) positioning the device within a chamber and loosely connecting an end of the device with a port such that an annular passage is defined between the end and the port;

(b) spraying a washing solution over the device from nozzles within the chamber to remove soil from exterior surfaces of the device and supplying the washing solution to the port, a large portion of the washing solution flowing into the internal passage of the device to remove soil from the internal passage of the device and a smaller portion flowing along the annular passage; and (c) spraying a microbial decontaminant solution over the device from nozzles within the chamber to microbially decontaminate the exterior surfaces of the device, supplying the microbial decontaminant solution to the internal passage of the device to microbially decontaminate the internal passage of the device and concurrently flowing a portion of the decontaminant solution through the annular passage between the device and a solution supply port into the chamber; and (d) spraying a sterile rinse fluid over the device from nozzles within the chamber to rinse the exterior surfaces of the device.

17. The method of claim 15, further including, after step (d):
   blowing air from nozzles within the chamber over exterior surfaces of the device; and
   delivering air to the lumen of the endoscope.

18. The method of claim 17, further including, after step (b):
   blowing air from nozzles within the chamber over exterior surfaces of the endoscope; and
   delivering air to the lumen of the endoscope.

19. The method of claim 1, further including, between steps (b) and (c):
   spraying a pretreatment solution over the device which includes at least one of a buffering agent and a corrosion inhibitor.

20. The method of claim 19, wherein the pretreatment solution includes a buffering agent, a corrosion inhibitor, and a surfactant.

21. A method of cleaning and microbially decontaminating a device comprising the sequential steps of:
   (a) positioning the device with an internal passage within a chamber and connecting the internal passage to a fluid port;
   (b) spraying a washing solution over the device from nozzles within the chamber to remove soil from exterior surfaces of the device;
   (c) draining the washing solution and microbial contamination washed from the device from the chamber to reduce bioload;
   (d) spraying a pretreatment solution which includes at least one of a buffering agent and a corrosion inhibitor over the device and delivering the pretreatment solution through the fluid port to the internal passage of the device;
   (e) after step (d), spraying a microbial decontaminant solution over the device and delivering the microbial decontaminant through the fluid port to microbially decontaminate the exterior surfaces and the internal passage of the device; and
   (f) spraying a sterile rinse fluid over the device from nozzles within the chamber to rinse the exterior surfaces of the device.

22. The method of claim 21, further including, prior to the step of spraying the pretreatment solution over the device:
   rinsing the device to remove the washing solution.

23. The method of claim 21, further including, after the step of spraying the pretreatment solution and prior to step (e):
   combining the pretreatment solution with an antimicrobial decontaminant to form the decontaminant solution.

24. A method of cleaning and microbially decontaminating a device -comprising the sequential steps of:
   (a) positioning the device within a chamber;
   (b) spraying a washing solution over the device from nozzles within the chamber to remove soil from exterior surfaces of the device;
   (c) spraying a microbial decontaminant solution over the device from nozzles within the chamber to microbially decontaminate the exterior surfaces of the device and draining the microbial decontaminant solution;
   (d) forming a sterile rinse fluid in a water heater by heating unsterile water to a sufficient temperature to sterilize the water;
   (e) flowing the sterile rinse fluid from the water heater to nozzles within the chamber through fluid lines which interconnect the water heater and the nozzles; and
   (f) spraying the sterile rinse fluid over the device from the nozzles to rinse the exterior surfaces of the device.

25. A method of cleaning and microbially decontaminating a device comprising the sequential steps of:
   (a) positioning the device within a chamber;
   (b) spraying a washing solution over the device from nozzles within the chamber to remove soil from exterior surfaces of the device;
   (c) spraying a microbial decontaminant solution over the device from nozzles within the chamber to microbially decontaminate the exterior surfaces of the device and draining the microbial decontaminant solution;
   (d) forming a sterile rinse fluid in a water heater by heating unsterile water to a sufficient temperature to sterilize the water;
   (e) removing salts from the sterile rinse water;
   (f) flowing the sterile rinse fluid from the water heater to nozzles within the chamber through fluid lines which interconnect the water heater and the nozzles; and
   (g) spraying the sterile rinse fluid over the device from the nozzles to rinse the exterior surfaces of the device.

26. The method of claim 1, wherein the decontaminant solution includes peracetic acid.

27. The method of claim 26, further including, during step (c):
   monitoring the concentration of peracetic acid in the decontaminant solution.

28. A method of cleaning and microbially decontaminating a device comprising the sequential steps of:
   (a) positioning the device within a chamber;
   (b) spraying a washing solution over the device from nozzles within the chamber to remove soil from the device;
   (c) spraying a microbial decontaminant solution which includes peracetic acid over the device from nozzles within the chamber to microbially decontaminate the device; and
   (d) during step (c), monitoring a concentration of peracetic acid in the decontaminant solution and, if the concentration of peracetic acid falls below a predetermined level, performing at least one of:
   terminating the method;
   signaling that the peracetic acid is below the predetermined level;
   adding additional peracetic acid to the decontaminant solution; and
   extending step (c) for a sufficient period of time to microbially decontaminate the exterior surfaces at the monitored peracetic acid concentration.

29. A method of microbially decontaminating a device comprising the sequential steps of:
   (a) loading the device into a chamber through an opening;
   (b) sealing the opening with a door;
   (c) moving a latching mechanism from an unlatched position, in which the latching mechanism allows opening of the door, to a latching position, in which the latching mechanism holds the door in a sealing relationship across the access opening latching the door;
   (d) moving a locking mechanism from an unlocked position, in which the locking mechanism allows unlatching of the latching mechanism, to a locked position, in which the locking mechanism locks the latching mechanism, preventing opening of the door; and (e) after steps (c) and (d), spraying a microbial decontaminant solution over the device from nozzles within the chamber to microbially decontaminate the exterior surfaces of the device.

30. A method of microbially decontaminating a device comprising the-sequential steps of:

(a) loading the device into a chamber through an opening;

(b) sealing the opening with a door;

(c) moving a latching mechanism from an unlatched position, in which the latching mechanism allows opening of the door, to a latching position, in which the latching mechanism holds the door in a sealing relationship across the access opening latching the door;

(d) after step (c), automatically sensing that the door is in the latching position;

(e) after step (d), moving a locking mechanism from an unlocked position, in which the locking mechanism allows unlatching of the latching mechanism, to a locked position, in which the locking mechanism locks the latching mechanism, preventing opening of the door;

(f) after step (e), spraying a microbial decontaminant solution over the device within the chamber to microbially decontaminate the device; and (g) controlling the locking mechanism during step (f) to ensure that the locking mechanism does not move to the unlocked position until step (f) is complete and after step (f), releasing the locking mechanism permitting the door to be unlatched.

31. The method of claim 29, wherein the step of moving the latching mechanism to the latching position includes:

pivoting an arm connected with an exterior of the chamber until a roller, rotatably connected to the arm, engages an engagement member on an outer surface of the door.

32. The method of claim 31, wherein the step of moving the locking mechanism to the locked position further includes:

engaging the arm with a rod which prevents pivoting of the arm in the locked position.

33. The method of claim 29, further including:

automatically sensing that the locking mechanism is in the locked position prior to commencing step (e).

* * * * *